US011744710B2

(12) United States Patent
Francis et al.

(10) Patent No.: US 11,744,710 B2
(45) Date of Patent: Sep. 5, 2023

(54) IMPLANTABLE NUCLEAR PROSTHESIS, KITS, AND RELATED METHODS

(71) Applicant: SPINAL STABILIZATION TECHNOLOGIES, LLC, San Antonio, TX (US)

(72) Inventors: W. Loren Francis, Erie, CO (US); Mark A. Novotny, Frisco, CO (US); Cory R. A. Hallam, San Antonio, TX (US); Jake Ganem, Cape Neddick, ME (US)

(73) Assignee: SPINAL STABILIZATION TECHNOLOGIES LLC, San Antonio, TX (US)

( * ) Notice: Subject to any disclaimer, the term of this patent is extended or adjusted under 35 U.S.C. 154(b) by 11 days.

(21) Appl. No.: 16/560,684

(22) Filed: Sep. 4, 2019

(65) Prior Publication Data
US 2020/0113705 A1 Apr. 16, 2020

Related U.S. Application Data

(60) Provisional application No. 62/726,704, filed on Sep. 4, 2018.

(51) Int. Cl.
*A61F 2/44* (2006.01)
*A61F 2/46* (2006.01)
(Continued)

(52) U.S. Cl.
CPC ............. *A61F 2/441* (2013.01); *A61F 2/442* (2013.01); *A61F 2/4611* (2013.01);
(Continued)

(58) Field of Classification Search
CPC ........ A61F 2/441; A61F 2/442; A61F 2/4611; A61F 2002/30548; A61F 2002/3008;
(Continued)

(56) References Cited

U.S. PATENT DOCUMENTS 3,875,595 A 4/1975 Froning
4,187,390 A 2/1980 Gore
(Continued)

FOREIGN PATENT DOCUMENTS

CA 2468908 6/2003
CN 101076302 A 11/2007
(Continued)

OTHER PUBLICATIONS

Birkenmaier et al., "Minimally Invasive Endoscopic Spinal Surgery", www.pineuniverse.com/displayarticle.pho/article2016.html.
(Continued)

*Primary Examiner* — Bruce E Snow
(74) *Attorney, Agent, or Firm* — Norton Rose Fulbright US LLP

(57) ABSTRACT

The present disclosure includes devices, apparatuses, kits, and methods for replacing a nucleus pulposus of an intervertebral disc with an implantable nuclear prosthesis filled with a curable silicone material in situ. Configurations of the present spinal implant devices include a flexible body defining an outer fillable enclosure that defines an outer chamber, an inner fillable enclosure that defines an inner chamber, and a proximal plug configured to be coupled to the inner fillable enclosure.

25 Claims, 12 Drawing Sheets

(51) Int. Cl.
*A61F 2/30* (2006.01)
*A61M 25/10* (2013.01)

(52) U.S. Cl.
CPC .............. *A61F 2002/3008* (2013.01); *A61F 2002/30548* (2013.01); *A61F 2002/30583* (2013.01); *A61F 2002/30586* (2013.01); *A61M 2025/1013* (2013.01); *A61M 2025/1079* (2013.01)

(58) Field of Classification Search
CPC ........... A61F 2002/30583; A61F 2002/30586; A61M 2025/1079; A61M 2025/1013; A61B 17/8855
See application file for complete search history.

(56) References Cited

U.S. PATENT DOCUMENTS

| | | | |
|---|---|---|---|
| 4,338,942 | A | 7/1982 | Fogarty |
| 4,478,898 | A | 10/1984 | Kato |
| 4,517,979 | A | 5/1985 | Pecenka |
| 4,619,641 | A | 10/1986 | Schanzer |
| 4,743,480 | A | 5/1988 | Campbell et al. |
| 5,123,926 | A | 6/1992 | Pisharodi |
| 5,152,782 | A | 10/1992 | Kowligi et al. |
| 5,181,921 | A | 1/1993 | Makita et al. |
| 5,192,310 | A | 3/1993 | Herweck et al. |
| 5,192,326 | A | 3/1993 | Bao et al. |
| 5,437,661 | A | 8/1995 | Rieser |
| 5,439,464 | A | 8/1995 | Shapiro |
| 5,466,509 | A | 11/1995 | Kowligi et al. |
| 5,571,189 | A | 11/1996 | Kuslich |
| 5,628,786 | A | 5/1997 | Banas et al. |
| 5,645,597 | A | 7/1997 | Krapiva |
| 5,674,295 | A | 10/1997 | Ray et al. |
| 5,702,449 | A | 12/1997 | McKay |
| 5,752,969 | A | 5/1998 | Cunci et al. |
| 5,827,327 | A | 10/1998 | McHaney et al. |
| 5,860,425 | A | 1/1999 | Benderev et al. |
| 5,865,845 | A | 2/1999 | Thalgott |
| 5,879,366 | A | 3/1999 | Shaw et al. |
| 5,888,220 | A | 3/1999 | Felt |
| 5,888,226 | A | 3/1999 | Rogozinski |
| 5,890,268 | A | 4/1999 | Mullen et al. |
| 5,910,277 | A | 6/1999 | Ishino et al. |
| 5,928,284 | A | 7/1999 | Mehdizadeh |
| 5,935,147 | A | 8/1999 | Kensey et al. |
| 5,954,767 | A | 9/1999 | Pajotin et al. |
| 5,972,022 | A | 10/1999 | Huxel |
| 5,976,174 | A | 11/1999 | Ruiz |
| 5,981,826 | A | 11/1999 | Ku et al. |
| 5,990,378 | A | 11/1999 | Ellis |
| 6,001,125 | A | 12/1999 | Golds et al. |
| 6,001,130 | A | 12/1999 | Bryan et al. |
| 6,007,570 | A | 12/1999 | Sharkey et al. |
| 6,007,575 | A | 12/1999 | Samuels |
| 6,019,793 | A | 2/2000 | Perren et al. |
| 6,036,724 | A | 3/2000 | Lentz et al. |
| 6,079,868 | A * | 6/2000 | Rydell .................... A61F 2/441 604/416 |
| 6,126,682 | A | 10/2000 | Sharkey et al. |
| 6,127,597 | A | 10/2000 | Beyar |
| 6,140,452 | A | 10/2000 | Felt et al. |
| 6,146,419 | A | 11/2000 | Eaton |
| 6,180,848 | B1 | 1/2001 | Flament et al. |
| 6,183,518 | B1 | 2/2001 | Ross et al. |
| 6,206,921 | B1 | 3/2001 | Guagliano et al. |
| 6,224,630 | B1 | 5/2001 | Bao et al. |
| 6,248,131 | B1 | 6/2001 | Felt et al. |
| 6,264,695 | B1 | 7/2001 | Stoy |
| 6,332,894 | B1 | 12/2001 | Stalcup et al. |
| 6,344,054 | B1 | 2/2002 | Parodi |
| 6,361,637 | B2 | 3/2002 | Martin et al. |
| 6,375,682 | B1 | 4/2002 | Fleischmann et al. |
| 6,390,992 | B1 | 5/2002 | Morris et al. |
| 6,395,032 | B1 | 5/2002 | Gauchet |
| 6,398,803 | B1 | 6/2002 | Layne et al. |
| 6,402,750 | B1 | 6/2002 | Atkinson et al. |
| 6,419,704 | B1 | 7/2002 | Ferree |
| 6,428,576 | B1 | 8/2002 | Haldimann |
| 6,436,143 | B1 | 8/2002 | Ross et al. |
| 6,443,988 | B2 | 9/2002 | Felt et al. |
| 6,482,234 | B1 | 11/2002 | Weber et al. |
| 6,527,804 | B1 | 3/2003 | Gauchet et al. |
| 6,533,818 | B1 | 3/2003 | Weber et al. |
| 6,582,466 | B1 | 6/2003 | Gauchet |
| 6,596,008 | B1 | 7/2003 | Kambin |
| 6,632,235 | B2 | 10/2003 | Weikel et al. |
| 6,645,248 | B2 | 11/2003 | Casutt |
| 6,673,103 | B1 | 1/2004 | Golds et al. |
| 6,689,125 | B1 | 2/2004 | Keith et al. |
| 6,712,853 | B2 | 3/2004 | Kuslich |
| 6,733,532 | B1 | 5/2004 | Gauchet et al. |
| 6,733,533 | B1 | 5/2004 | Lozier |
| 6,780,497 | B1 | 8/2004 | Walter |
| 6,852,095 | B1 | 2/2005 | Ray |
| 6,852,223 | B2 | 2/2005 | Huang et al. |
| 6,866,681 | B2 | 3/2005 | Laboureau et al. |
| 6,893,465 | B2 | 5/2005 | Huang |
| 6,893,466 | B2 | 5/2005 | Trieu |
| 6,932,843 | B2 | 8/2005 | Smith et al. |
| 6,936,070 | B1 | 8/2005 | Muhanna |
| 6,958,077 | B2 | 10/2005 | Suddaby |
| 6,969,404 | B2 | 11/2005 | Ferree |
| 6,969,405 | B2 | 11/2005 | Suddaby |
| 6,984,246 | B2 | 1/2006 | Huang |
| 7,001,431 | B2 | 2/2006 | Bao et al. |
| 7,004,971 | B2 | 2/2006 | Serhan et al. |
| 7,008,427 | B2 | 3/2006 | Sevrain |
| 7,056,345 | B2 | 6/2006 | Kuslich |
| 7,077,865 | B2 | 7/2006 | Bao et al. |
| 7,133,001 | B2 | 11/2006 | Mrstik et al. |
| 7,156,861 | B2 | 1/2007 | Scribner et al. |
| 7,156,877 | B2 | 1/2007 | Lotz et al. |
| 7,182,783 | B2 | 2/2007 | Trieu |
| 7,201,751 | B2 | 4/2007 | Zucherman et al. |
| 7,201,776 | B2 | 4/2007 | Ferree et al. |
| 7,204,851 | B2 | 4/2007 | Trieu et al. |
| 7,220,282 | B2 | 5/2007 | Kuslich |
| 7,267,687 | B2 | 9/2007 | McGuckin et al. |
| 7,273,497 | B2 | 9/2007 | Ferree |
| 7,297,158 | B2 | 11/2007 | Jensen |
| 7,309,359 | B2 | 12/2007 | Trieu et al. |
| 7,556,650 | B2 | 7/2009 | Collins et al. |
| 7,563,284 | B2 | 7/2009 | Coppes et al. |
| 7,618,461 | B2 | 11/2009 | Trieu |
| 7,632,291 | B2 | 12/2009 | Stephens et al. |
| 7,632,294 | B2 | 12/2009 | Milbodker et al. |
| 7,641,691 | B2 | 1/2010 | Lotz et al. |
| 7,645,301 | B2 * | 1/2010 | Hudgins .................. A61F 2/441 623/17.11 |
| 7,713,301 | B2 | 5/2010 | Bao et al. |
| 7,722,612 | B2 | 5/2010 | Sala et al. |
| 7,731,753 | B2 | 6/2010 | Reo et al. |
| 7,766,965 | B2 | 8/2010 | Bao et al. |
| 7,789,913 | B2 | 9/2010 | Collins et al. |
| 7,799,079 | B2 | 9/2010 | Hestad et al. |
| 7,837,733 | B2 | 11/2010 | Collins et al. |
| 7,842,055 | B2 | 11/2010 | Pintor et al. |
| 7,896,920 | B2 | 3/2011 | Yuksel et al. |
| 7,931,689 | B2 | 4/2011 | Hochschuler et al. |
| 7,947,079 | B2 | 5/2011 | Helm et al. |
| 7,972,351 | B2 | 7/2011 | Trinidad |
| 7,993,351 | B2 | 8/2011 | Worley et al. |
| 7,993,404 | B2 | 8/2011 | Trieu |
| 7,998,210 | B2 | 8/2011 | Edie et al. |
| 8,012,210 | B2 | 9/2011 | Lin et al. |
| 8,012,211 | B2 | 9/2011 | Kuslich |
| 8,043,381 | B2 | 10/2011 | Hestad et al. |
| 8,066,758 | B2 | 11/2011 | Bogert et al. |
| 8,083,800 | B2 | 12/2011 | Edie |
| 8,092,536 | B2 | 1/2012 | Ahrens et al. |
| 8,100,978 | B2 | 1/2012 | Bass |
| 8,123,808 | B2 | 2/2012 | Dewey et al. |

(56) References Cited

U.S. PATENT DOCUMENTS

| | | |
|---|---|---|
| 8,133,250 B2 | 3/2012 | Parsonage et al. |
| 8,142,456 B2 | 3/2012 | Rosqueta et al. |
| 8,142,489 B2 | 3/2012 | Doran et al. |
| 8,236,057 B2 | 8/2012 | Wirtel, III et al. |
| 8,246,682 B2 | 8/2012 | Slivka et al. |
| 8,287,595 B2 | 10/2012 | Vresilovic et al. |
| 8,292,961 B2 | 10/2012 | Osman |
| 8,317,864 B2 | 10/2012 | Kim |
| 8,337,556 B2 | 12/2012 | Shaolian et al. |
| 8,337,557 B2 | 12/2012 | Collins et al. |
| 8,349,013 B2 | 1/2013 | Zucherman et al. |
| 8,377,131 B2 | 2/2013 | Lin |
| 8,377,136 B2 | 2/2013 | Simonton |
| 8,377,138 B2 | 2/2013 | Reo et al. |
| 8,382,838 B2 | 2/2013 | Baumgartner et al. |
| 8,398,511 B2 | 3/2013 | Sandusky |
| 8,403,987 B2 | 3/2013 | Reo et al. |
| 8,419,839 B2 | 4/2013 | Shimatani |
| 8,444,694 B2 | 5/2013 | Collins et al. |
| 8,449,660 B2 | 5/2013 | Shimatani et al. |
| 8,454,612 B2 | 6/2013 | Lambrecht et al. |
| 8,460,383 B2 | 6/2013 | Wirtel, III et al. |
| 8,480,718 B2 | 7/2013 | Protopsaltis et al. |
| 8,540,772 B2 | 9/2013 | Osman |
| 8,551,172 B2 | 10/2013 | Park |
| 8,562,634 B2 | 10/2013 | Middleton |
| 8,603,171 B2 | 12/2013 | McClellan, III et al. |
| 8,632,592 B2 | 1/2014 | Barrall |
| 8,636,803 B2 | 1/2014 | Hibri et al. |
| 8,663,328 B2 | 3/2014 | Justis et al. |
| 8,690,919 B2 | 4/2014 | Lange et al. |
| 8,727,920 B2 | 5/2014 | Sandusky |
| 8,734,459 B1 | 5/2014 | Alobaid |
| 8,747,475 B2 | 6/2014 | Kuslich |
| 8,808,381 B2 | 8/2014 | Kim et al. |
| 8,888,850 B2 | 11/2014 | Linares |
| 8,894,563 B2 | 11/2014 | Connors et al. |
| 8,945,223 B2 | 2/2015 | Trieu |
| 8,979,931 B2 | 3/2015 | Stad et al. |
| 9,486,323 B1 | 11/2016 | Hibri et al. |
| 2002/0026244 A1 | 2/2002 | Trieu |
| 2002/0068975 A1 | 6/2002 | Teitelbaum et al. |
| 2002/0147497 A1 | 10/2002 | Belef et al. |
| 2002/0151979 A1 | 10/2002 | Lambrecht et al. |
| 2002/0198588 A1 | 12/2002 | Armstrong et al. |
| 2003/0028251 A1 | 2/2003 | Mathews |
| 2003/0040772 A1 | 2/2003 | Hyodoh et al. |
| 2003/0114917 A1 | 6/2003 | Holloway et al. |
| 2003/0153976 A1 | 8/2003 | Cauthen et al. |
| 2003/0199979 A1 | 10/2003 | McGuckin, Jr. |
| 2004/0106999 A1 | 6/2004 | Mathews |
| 2004/0186471 A1 | 9/2004 | Trieu |
| 2004/0220672 A1 | 11/2004 | Shadduck |
| 2004/0230309 A1 | 11/2004 | DiMauro et al. |
| 2005/0004578 A1 | 1/2005 | Lambrecht et al. |
| 2005/0015047 A1 | 1/2005 | Shah |
| 2005/0015150 A1 | 1/2005 | Lee |
| 2005/0055099 A1 | 3/2005 | Ku |
| 2005/0065609 A1 | 3/2005 | Wardlaw |
| 2005/0090901 A1 | 4/2005 | Studer |
| 2005/0119752 A1 | 6/2005 | Williams et al. |
| 2005/0119852 A1 | 6/2005 | Iguchi et al. |
| 2005/0137675 A1 | 6/2005 | Dubson et al. |
| 2005/0197702 A1 | 9/2005 | Coppes et al. |
| 2005/0251259 A1 | 11/2005 | Suddaby |
| 2005/0278029 A1 | 12/2005 | Trieu |
| 2006/0047296 A1 | 3/2006 | Embry et al. |
| 2006/0149380 A1 | 7/2006 | Lotz et al. |
| 2006/0247780 A1 | 11/2006 | Bert |
| 2006/0253132 A1 | 11/2006 | Evans et al. |
| 2006/0265077 A1 | 11/2006 | Zwirkoski |
| 2006/0293749 A1 | 12/2006 | Hudgins et al. |
| 2007/0060924 A1 | 3/2007 | Choi |
| 2007/0073402 A1 | 3/2007 | Vresilovic et al. |
| 2007/0093906 A1 | 4/2007 | Hudgins et al. |
| 2007/0135921 A1 | 6/2007 | Park |
| 2007/0150061 A1 | 6/2007 | Trieu |
| 2007/0162135 A1 | 7/2007 | Segal et al. |
| 2007/0162136 A1 | 7/2007 | O'Neil et al. |
| 2007/0168031 A1 | 7/2007 | Hudgins et al. |
| 2007/0168042 A1 | 7/2007 | Hudgins et al. |
| 2007/0173935 A1 | 7/2007 | O'Neil et al. |
| 2007/0173940 A1 | 7/2007 | Hestad et al. |
| 2007/0200271 A1 | 8/2007 | Dave |
| 2007/0213732 A1 | 9/2007 | Khanna et al. |
| 2007/0255285 A1 | 11/2007 | Trieu |
| 2007/0255406 A1 | 11/2007 | Trieu |
| 2007/0265077 A1 | 11/2007 | Tom et al. |
| 2007/0270953 A1 | 11/2007 | Trieu |
| 2007/0288095 A1 | 12/2007 | Wirtel et al. |
| 2008/0046082 A1 | 2/2008 | Lee |
| 2008/0058932 A1 | 3/2008 | Trieu et al. |
| 2008/0119943 A1 | 5/2008 | Armstrong et al. |
| 2008/0132934 A1 | 6/2008 | Reiley et al. |
| 2008/0154367 A1 | 6/2008 | Justis et al. |
| 2008/0154368 A1 | 6/2008 | Justis et al. |
| 2008/0154373 A1 | 6/2008 | Protopsaltis et al. |
| 2008/0195210 A1 | 8/2008 | Milijasevic et al. |
| 2008/0288073 A1 | 11/2008 | Renganath et al. |
| 2008/0288074 A1 | 11/2008 | O'Neil et al. |
| 2009/0012618 A1 | 1/2009 | Ahrens et al. |
| 2009/0030399 A1 | 1/2009 | Raiszadeh et al. |
| 2009/0076609 A1 | 3/2009 | Stewart |
| 2009/0076610 A1 | 3/2009 | Afzal |
| 2009/0082870 A1 | 3/2009 | Osman |
| 2009/0105823 A1 | 4/2009 | Williams et al. |
| 2009/0112221 A1 | 4/2009 | Burke et al. |
| 2009/0112323 A1 | 4/2009 | Hestad et al. |
| 2009/0118833 A1 | 5/2009 | Hudgins et al. |
| 2009/0163994 A1 | 6/2009 | Quigley et al. |
| 2009/0222093 A1 | 9/2009 | Liu et al. |
| 2009/0240341 A1 | 9/2009 | Diwan et al. |
| 2009/0299476 A1 | 12/2009 | Diwan et al. |
| 2010/0030216 A1 | 2/2010 | Arcenio |
| 2010/0191335 A1 | 7/2010 | Root et al. |
| 2010/0193999 A1 | 8/2010 | Anneaux et al. |
| 2010/0256619 A1 | 10/2010 | Teitelbaum et al. |
| 2010/0256766 A1 | 10/2010 | Hibri et al. |
| 2010/0292798 A1 | 11/2010 | Maestretti |
| 2011/0093076 A1 | 4/2011 | Reo et al. |
| 2011/0125158 A1 | 5/2011 | Diwan et al. |
| 2011/0190753 A1 | 8/2011 | Forrest |
| 2011/0196499 A1 | 8/2011 | Boucher et al. |
| 2011/0264224 A1 | 10/2011 | Ferree |
| 2011/0282418 A1 | 11/2011 | Saunders et al. |
| 2011/0319996 A1 | 12/2011 | Barrall |
| 2012/0089227 A1 | 4/2012 | Jarzem |
| 2012/0089229 A1 | 4/2012 | Thramann |
| 2012/0165941 A1 | 6/2012 | Rabiner et al. |
| 2012/0277862 A1 | 11/2012 | Tornier et al. |
| 2012/0310352 A1 | 12/2012 | DiMauro et al. |
| 2012/0316648 A1 | 12/2012 | Lambrecht et al. |
| 2013/0004586 A1 | 1/2013 | Vachon et al. |
| 2013/0103155 A1 | 4/2013 | Tornier et al. |
| 2013/0131806 A1 | 5/2013 | Carpetner |
| 2013/0297026 A1 | 11/2013 | de Villiers et al. |
| 2013/0304212 A1 | 11/2013 | VonGunten |
| 2014/0052250 A1 | 2/2014 | Wirtel et al. |
| 2014/0094914 A1 | 4/2014 | Hibri et al. |
| 2014/0276832 A1 | 9/2014 | Hibri et al. |
| 2014/0277467 A1 | 9/2014 | Hibri et al. |
| 2014/0288656 A1 | 9/2014 | Kuslich |
| 2015/0057752 A1 | 2/2015 | Hibri et al. |
| 2016/0120653 A1* | 5/2016 | Hibri ............... A61F 2/441 |
| | | 29/525.01 |
| 2016/0120654 A1 | 5/2016 | Hibri et al. |
| 2017/0056195 A1* | 3/2017 | Lutz ............... A61F 2/441 |
| 2017/0246005 A1* | 8/2017 | Hibri ............... A61F 2/442 |

FOREIGN PATENT DOCUMENTS

| | | |
|---|---|---|
| CN | 101448471 | 6/2009 |
| CN | 101557779 A | 10/2009 |
| CN | 103099689 | 5/2013 |

(56) References Cited

FOREIGN PATENT DOCUMENTS

| | | |
|---|---|---|
| JP | 2005511143 | 4/2005 |
| KR | 20120040309 | 4/2012 |
| WO | WO-0197721 A2 * | 12/2001 ......... A61B 17/1631 |
| WO | WO 2003/047472 | 6/2003 |
| WO | WO 2006/060482 | 12/2005 |
| WO | WO 2006/025815 | 3/2006 |
| WO | WO 2006/130796 | 12/2006 |
| WO | WO 2007/087404 | 8/2007 |
| WO | WO 2014/158762 | 10/2014 |
| WO | WO 2016/073587 | 5/2016 |

OTHER PUBLICATIONS

Examination Report No. 1 from IP Australia issued in corresponding Patent Application No. 2016315964 dated May 23, 2020.
International Search Report and Written Opinion for PCT/US2015/058976 dated Jan. 25, 2016.
International Search Report and Written Opinion for PCT/US2015/059011, dated Feb. 15, 2016.
International Search Report and Written Opinion issued in PCT Application No. PCT/US2016/049816, dated Dec. 8, 2016.
International Search Report dated Jun. 17, 2014 for International Application No. PCT/US2014/019911, filed Mar. 3, 2014.
International Search Report dated Jun. 19, 2014 for International Application No. PCT/US2014/019887.
International Search Report dated Jun. 25, 2014 for International Application No. PCT/US2014/019957, filed Mar. 3, 2014.
Office Action issued in Chinese Patent Application No. 201580066464.5, dated Aug. 2, 2018. Received Aug. 22, 2018.
Office Action Issued in Corresponding Brazilian Patent Application No. BR112015023003-2, dated Jan. 22, 2020.
Office Action issued in Corresponding Canadian Application No. 2,906,340, dated Mar. 3, 2020.
Search Report from China National Intellectual Property Administration issued in corresponding Patent Application No. 201680058105X dated Apr. 23, 2020.
Sharma et al., "Manufacturing of Doubly Curved Tubular Composite Structure: Mapping and Weave Modification," *Thermoplastic Composite Materials*, 15:209-225 (May 2002).
Supplementary European Search Report issued in European Application No. 15857214.9, dated Oct. 10, 2017.
The First Office Action from the China National Intellectual Property Administration issued in corresponding Patent Application No. 201680058105X dated Apr. 30, 2020.
Viscocliosi et al., "Beyond Total Disc: The Future of Spine Surgery," *Spine Non-Fusion, Musculoskeletal Investment Research*, pp. 1-289, (May 2004).
Wu et al., "The direct effect of graft compliance mismatch per se on development of host arterial intimal hyperplasia at the anastomotic interface," *Annals of Vascular Surgery*, 7(2):156-168 (Mar. 1993).
International Search Report and Written Opinion from the International Searching Authority issued in corresponding International application No. PCT/US2019/049548 dated May 7, 2021.
Extended European Search Report issued in Corresponding European Application No. 19886958.8, dated Jul. 7, 2022.

* cited by examiner

IMPLANTABLE NUCLEAR PROSTHESIS, KITS, AND RELATED METHODS

CROSS-REFERENCE TO RELATED APPLICATIONS

This application claims the benefit of priority of U.S. Provisional Patent Application No. 62/726,704, filed Sep. 21, 2018. The contents of which the above-referenced application is specifically incorporated herein by reference without disclaimer.

TECHNICAL FIELD

The present application relates generally to devices, kits, and methods for replacing an intervertebral disc, and more particularly, but not by way of limitation, to an implantable disc replacement which may be implanted using minimally invasive surgical techniques or percutaneously, and methods for manufacturing such a disc replacement/prosthesis.

BACKGROUND

An estimated 4.1 million Americans suffer from intervertebral disc disorders or low-back disabilities. Although the cause of low-back pain is multifactorial, defects in intervertebral discs are generally considered to be a primary source or an initiating factor that leads to altered spinal biomechanical function and non-physiologic stress in the surrounding tissues.

The intervertebral disc consists of three distinct parts: the nucleus pulposus; the annulus fibrosus; and the cartilaginous endplates. The nucleus pulposus is a viscous, mucoprotein gel centrally located within the disc and contains sulfated glycosaxninoglycans in a loose network of type II collagen fibers. The water content of the nucleus pulposus, approximately 80% at birth, gradually decreases with age and contributes to the degeneration of the disc as part of the aging process. The annulus fibrosus is the portion of the intervertebral disc that forms the outer boundary of the intervertebral disc, and is made up of coarse type I collagen fibers oriented obliquely and arranged in lamellae which attach the adjacent vertebral bodies. The type I collagen fibers extend in the same direction within a given lamella, but opposite to those in adjacent lamellae. The overall collagen content of the intervertebral disc steadily increases from the center of the nucleus pulposus to the outer layers of the annulus fibrosus, where collagen can reach 70% or more of the dry weight of the intervertebral disc. The cartilaginous vertebral end plates, which contain hyaline cartilage, cover the end surfaces of the vertebral bodies and serve as the cranial and caudal surfaces of the intervertebral disc.

The ability of the intervertebral disc to attract and retain water gives it unique structural properties. For example, the proteoglycans of the nucleus pulposus attract water osmotically, exerting a swelling pressure that enables the intervertebral disc to support compressive loads. The pressurized nucleus pulposus also creates significant tensile pre-stress within the annulus fibrosus and ligamentous structures surrounding the intervertebral disc. This results in an annular architecture where the collagen fibers are oriented approximately 60° relative to the longitudinal axis of the spine to optimally support the tensile stresses developed within the spine. This tissue pre-stress, and maintaining the integrity of the annulus fibrosus, contributes significantly to normal kinematics and mechanical response of the human spine.

When the physical stress placed on the spine exceeds the nuclear swelling pressure, water is expressed from the intervertebral disc through the semipermeable cartilaginous end plates. This loss of nuclear water negatively affects the load distribution internal to the intervertebral disc. In a healthy disc under compressive loading, circumferential hoop stress is carried mainly by the annulus fibrosus. After extended compressive loading, pressure distribution changes such that the highest axial compressive stress occurs in the posterior annulus fibrosus. Similar pressure distribution changes have been noted in degenerated and denucleated intervertebral discs as well. This reversal in the state of annular stress demonstrates that nuclear dehydration significantly alters stress distributions within the intervertebral disc as well as its biomechanical response to loading.

Chemical changes are also observed with degeneration, particularly the loss of proteoglycan and water. This dehydration contributes to the loss of intervertebral disc height. Secondary changes in the annulus fibrosus include fibrocartilage production with disorganization of the lamellar architecture and increases in type II collagen.

Currently, there are few clinical options to offer patients who suffer from these conditions. The typical clinical options include conservative therapy with physical rehabilitation and surgical intervention with possible disc removal and spinal fusion for those who have failed more conservative therapy. Further, the existing techniques for forming a nuclear prosthesis in situ have not achieved convincing clinical acceptance or commercial success. One problem identified by the present disclosure is the substantial difference in the modulus of elasticity between the vertebral bony elements, including the vertebral end plates, and the annulus fibrosus on the one hand, and the implanted elements on the other. The high modulus of elasticity of the implanted material is disadvantageous since it does not dampen impacts or sudden increases in intra-discal pressure during extreme bending or torsion, especially during high loading peaks. The large difference in the modulus of elasticity between implanted disc materials and adjacent tissues can also lead to softening of the vertebral end plates and adjacent bone (spongeosus), resulting in subsidence of the nuclear implant. Migration and expulsion of the implant can also occur, particularly when there are defects in the annulus fibrosus. Confirmation of the proper size and orientation of the implant can also pose difficulty when replacing the nucleus pulposus with a nuclear prosthesis formed in situ.

Therefore, there is a need for an improved treatment for repacing or replacing degenerated discs. The present disclosure satisfies that need, as well as others, and overcomes the deficiencies associated with prior implants and treatment methods.

SUMMARY

This disclosure includes configurations of devices, apparatuses, and methods for replacing a nucleus pulposus of an intervertebral disc with an implantable nuclear prosthesis. Non-limiting examples of conditions that benefit from this disclosure include, but are not limited to, degenerative disc disease and spinal disc injuries caused by trauma.

For example, at least some of the present configurations include a kit for implanting a nuclear prosthesis. The kit includes a spinal implant device having a flexible body defining an outer fillable enclosure that defines an outer chamber having a body aperture; and an inner fillable enclosure defining an inner chamber such that the outer fillable enclosure at least partially surrounds the inner fillable enclosure, the inner fillable enclosure having an opening in fluid communication with the inner chamber; a proximal plug configured to be coupled to the inner fillable enclosure such that the proximal plug controls fluid communication through the opening; an inflation stylet configured to mate with the proximal plug and extend at least partially through the proximal plug, the inflation stylet having a first lumen configured to deliver a fluid to and remove a fluid from the inner chamber, and a second lumen at least partially surrounding the first lumen and configured to deliver a fluid to the outer chamber.

In some configurations of the present kits, the inflation stylet further includes an inflation tip for delivering fluid to the outer chamber. The inflation tip can be configured to be coupled to a distal end of the inflation stylet.

In some configurations of the present kits, the inner chamber has a proximal end with a proximal opening and a distal end with a distal opening.

In some configurations of the present kits, the outer fillable enclosure and inner fillable enclosure are axially symmetric around a longitudinal axis.

In some configurations of the present kits, the flexible body further defines a proximal opening in fluid communication with the inner chamber.

In some configurations of the present kits, the flexible body further defines a distal opening in fluid communication with the inner chamber.

In some configurations of the present kits, the proximal plug defines a receptacle configured to receive a portion of the inflation stylet and a plug aperture in fluid communication with the outer chamber when aligned with the body aperture.

In some configurations of the present kits, the proximal plug includes a re-sealable membrane to control fluid communication through the proximal opening of the inner chamber.

In some configurations of the present kits, the spinal implant device further includes a distal plug that seals the distal opening.

In some configurations of the present kits, the inflation stylet further includes a vent lumen in fluid communication with the second lumen.

In some configurations of the present kits, the spinal implant device further includes a first radiopaque marker (e.g., tantalum marker bead) coupled to either the distal plug or a portion of the flexible body that is closer to the distal opening of the inner chamber than to the proximal opening of the inner chamber.

In some configurations of the present kits, the spinal implant device further includes a second radiopaque marker (e.g., tantalum marker bead) coupled to either the proximal plug or a portion of the flexible body that is closer to the proximal opening of the inner chamber than to the distal opening of the inner chamber.

In some configurations of the present kits, the kit further contains one or more imaging balloons configured to assess a nuclectomy, interrogate an enucleated intervertebral disc cavity, and/or determine a size and a fill volume for the spinal implant device.

In some configurations of the present kits, the kit contains at least one imaging balloon with a durometer between Shore 10A and Shore 100A.

In some configurations of the present kits, the kit contains a second imaging balloon with a durometer greater than the durometer of the first imaging balloon.

In some configurations of the present kits, the kit further contains a delivery sheath surrounding the inflation stylet, where the delivery sheath is movable from a delivery position to a deployed position.

In some configurations of the present kits, the kit further contains a curable silicone material for injection into the outer chamber.

In some configurations of the present kits, the curable silicone material contains a radiographic material.

In some configurations of the present kits, the radiographic material contains 8 to 16 wt. % of barium sulfate.

In some configurations of the present kits, the curable silicone material substantially cures within ten minutes.

In some configurations of the present kits, the kit further includes a spinal disc access device.

In some configurations of the present kits, the kit further includes a spinal implant fill device comprising: a dispenser gun for injecting fluid into the outer chamber; a dual-syringe barrel; and a mixing tip.

In some configurations of the present kits, the kit further includes an inflation pressure gauge.

At least some of the present configurations of the devices include, a spinal implant device having a flexible body defining an outer fillable enclosure that defines an outer chamber having a body aperture; an inner fillable enclosure that defines an inner chamber such that the outer fillable enclosure at least partially surrounds the inner fillable enclosure, the inner fillable enclosure having an opening in fluid communication with the inner chamber; and a proximal plug configured to be coupled to the inner fillable enclosure such that the proximal plug controls fluid communication through the opening.

In some configurations, the inner chamber is configured to provide pressure feedback when the outer chamber is filled.

In some configurations, the spinal implant device has a durometer between Shore 10A and Shore 100A. In this way, the spinal implant device, when combined with a curable medium described below, can exhibit an elastic modulus capable of dampening impacts or sudden increases in intradiscal pressure during bending, torsion, and/or other high loading peak movements. In some configurations, the spinal implant device can further prevent spongeosus of adjacent bone and subsidence of the implant over time, thus mitigating migration and/or expulsion of the spinal implant device.

In some configurations, the flexible body comprises a coating containing one or more ingredients selected from the list of ingredients consisting of: drugs, bioactives, and/or stem cells. In this way, the spinal implant device can further enhance repair and/or restoration of physiologic function of the intervertebral disc. Other ingredients may be used to achieve certain desired properties and/or functions of the spinal implant device after implantation. The flexible body can also include a lubricious coating to aid in the delivery of the spinal implant device.

In some configurations of the present devices, the inner and outer fillable enclosures comprise a unitary piece of material.

In some configurations of the present devices, the inner chamber has a proximal end with a proximal opening and a distal end with a distal opening.

In some configurations of the present devices, the outer fillable enclosure and inner fillable enclosure are axially symmetric around a longitudinal axis. In this way, the spinal implant device will have a proper orientation in any direction when inserting the spinal implant device into an enucleated intervertebral disc cavity. Further, the axially symmetric shape of the outer fillable enclosure and inner fillable enclosure allows the spinal implant device to expand, when combined with a curable medium (e.g., curable silicone containing 12% barium sulfate), circumferentially around the longitudinal axis to fill the entire enucleated space by accounting for the expansion behavior of the curable medium.

In some configurations of the present devices, the flexible body further defines a proximal opening in fluid communication with the inner chamber.

In some configurations of the present devices, the flexible body further defines a distal opening in fluid communication with the inner chamber.

In some configurations of the present devices, the proximal plug defines a receptacle configured to receive a portion of an inflation stylet for delivering fluid to the inner and outer chambers and a plug aperture in fluid communication with the outer chamber when aligned with the body aperture. A proximal neck defined by the inner fillable enclosure may have features, such as grooves, for mating with matching features on the proximal plug to assist in locating proximal plug. The proximal plug may be inserted into and bonded with proximal neck. Proximal plug can also be configured to be coupled to an inflation tip of an inflation stylet.

In some configurations of the present devices, the inflation stylet includes an inflation tip for delivering fluid to the outer chamber. The inflation tip can be configured to be coupled to a distal end of the inflation stylet. Other configurations of the inflation stylet may omit one or more features, such as the inflation tip, and still achieve similar functions. For example, distal end of inflation stylet can be configured to be coupled to the proximal plug.

In some configurations of the present devices, the proximal plug includes a re-sealable membrane to control fluid communication through the proximal opening of the inner chamber. In this way, the re-sealable membrane prevents fluid from flowing around a first (contrast) lumen, described in further detail below, and into the outer chamber. The re-sealable membrane can also serve as a one-way valve and prevent any backflow of fluid from the inner chamber into the outer chamber when a fluid is delivered into the inner chamber. In this way, the inflation stylet, can be configured to communicate with the inner chamber and the outer chamber through a single opening and without the contents of each chamber mixing together.

In some configurations of the present devices, the spinal implant device further includes a distal plug that seals the distal opening. Other configurations of spinal implant device may omit one or more features, such as the distal plug, to achieve similar functions.

In some configurations of the present devices, the spinal implant device further includes a first radiopaque marker (e.g., tantalum marker bead) coupled to either the distal plug or a portion of the flexible body that is closer to the distal opening of the inner chamber than to the proximal opening of the inner chamber. Other configurations of spinal implant device may omit one or more features, such as the first radiopaque marker, to achieve similar functions.

In some configurations of the present devices, the spinal implant device further includes a second radiopaque marker (e.g., tantalum marker bead) coupled to either the proximal plug or a portion of the flexible body that is closer to the proximal opening of the inner chamber than to the distal opening of the inner chamber. Other configurations of spinal implant device may omit one or more features, such as the second radiopaque marker, to achieve similar functions.

In some configurations of the present devices, the outer chamber is filled with a curable silicone material.

In some configurations of the present devices, the curable silicone material contains a radiographic material.

In some configurations of the present devices, the radiographic material contains 8 to 16 wt. % of barium sulfate.

In some configurations of the present devices, the curable silicone material substantially cures within ten minutes.

In some configurations of the present devices, the spinal implant device further includes a retaining element for retaining the spinal implant device on an inflation stylet.

At least some of the present implementations include a method of replacing a nucleus pulposus of an intervertebral disc with a spinal implant device, the method including dilating the annulus fibrosus to gain access to an intervertebral disc. To preserve the integrity of the annulus fibrosus as much as possible, a guide pin (e.g., a K-wire) can be inserted into the annulus fibrosus and then a series of increasing diameter dilators can be placed over the guide pin. Once the desired diameter is obtained, an access cannula can be placed over the largest diameter dilator, and the dilator set can be removed. In this way, the integrity of the annulus fibrosus is substantially preserved through a controlled dilation that mitigates damage to the fibers in the annulus fibrosus and aids in promoting a successful deployment of the spinal implant device.

Proceeding to the next step, a nuclectomy is then performed under fluoroscopy to create an enucleated intervertebral disc cavity. Any one of the configurations of the presently disclosed spinal implant devices, including configurations of a dual-chambered spinal implant device, can then be inserted into the enucleated intervertebral disc cavity. The dual-chambered spinal implant device can have an inner chamber that is at least partially surrounded by an outer chamber, and configured such that the inner chamber, after being filled with a fluidic medium 220 (e.g., contrast medium), provides pressure feedback when the outer chamber is filled with a curable medium. An inflation stylet can be used to deliver the curable medium containing a radiopaque material (e.g., barium sulfate) to the outer chamber, thereby inflating the outer chamber to a threshold pressure (e.g., a working pressure that does not exceed 40 psi). The pressure feedback from the inner chamber can be monitored during delivery of the curable medium to ensure the threshold pressure is not exceeded. The curable medium is then allowed to cure and the fluidic medium 220 (e.g., contrast medium) from the inner chamber is then removed. In some configurations, the inner fillable enclosure is left vented so that fluids may enter and exit the inner fillable enclosure.

After performing the nuclectomy, an imaging balloon is inserted into the enucleated intervertebral disc cavity and inflated with a radiopaque fluid to assess completeness of the nuclectomy. The nuclectomy is repeated as needed to remove any remaining nucleus pulposus and the inflating and nuclectomy steps are repeated until the enucleated intervertebral disc cavity has been sufficiently enucleated.

In some implementations of the present methods, an imaging balloon is then inflated with a radiopaque fluid to interrogate the enucleated intervertebral disc cavity for defects and/or contraindications (e.g., tears in the annulus fibrosus, herniations, Schmorl's node, or other end plate defects). Once the user determines whether there are any defects and/or contraindications for implanting the spinal implant device, the imaging balloon is removed. In some implementations, the imaging balloon can have a durometer between Shore 10A and Shore 100A.

In some implementations of the present methods, if there are no defects and/or contraindications, the method proceeds by inserting a second imaging balloon having a durometer corresponding to a durometer of the spinal implant device or a durometer greater than the durometer of the first imaging balloon (if a first imaging balloon was used for previous steps). The second imaging balloon is then inflated with a radiopaque fluid to a threshold pressure and the volume of the radiopaque fluid is monitored to determine an approximate fill volume for the spinal implant device. The second imaging balloon is then imaged to determine a size for the spinal implant device and then removed. In some implementations, the same imaging balloon can be used for assessing the nuclectomy, interrogating the enucleated intervertebral disc cavity for defects and/or contraindications, and determining a size and fill volume for the spinal implant device.

At least some of the present implementations include imaging one or more views of the inflated imaging balloon; imaging one or more views of the spinal implant device corresponding to the one or more views imaged of the inflated imaging balloon; and, comparing the one or more views of the spinal implant device with the one or more views of the inflated imaging balloon to assess the spinal implant device. The one or more views of the inflated imaging balloon may be taken in a series of specified views. The one or more views of the imaging balloon and/or the one or more views of the spinal implant device may comprise indicia to quantify congruency between two of the same views. In this way, the position, orientation, and size of the spinal implant device can be confirmed manually.

The imaging and comparing steps may be performed electronically, and may include the step of automatically determining a percentage of overlap between two views. In this way, the position, orientation, and size of the spinal implant device can be confirmed automatically with software suited for determining the percentage of overlap between two views. Using software to automatically image and compare can provide certain advantages such as reduced surgical time and a more effective deployment of the spinal implant device. Further, automatically determining a percentage of overlap between two views can be particularly suited for use with robotic surgery and/or robotics-assisted surgery to insert the spinal implant device. A three-dimensional model may be generated from a first set of views of the imaging balloon and/or a second set of views of the spinal implant device. The three-dimensional model of the imaging balloon and/or the three-dimensional model of the spinal implant device may be used to estimate a fill volume for the spinal implant device. The three-dimensional model of the imaging balloon and/or the three-dimensional model of the spinal implant device may be used to determine a percentage of overlap. In this way, confirmation of the implantation of a spinal implant device can be obtained.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any configuration or implementation of the present devices, apparatuses, kits, and methods, the term "substantially" may be substituted with "within [a percentage] of" what is specified, where the percentage includes 0.1, 1, 5, and/or 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus, device, or kit that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Further, an apparatus, device, or structure that is configured in a certain way is configured in at least that way, but it can also be configured in other ways than those specifically described.

Any configuration or implementation of any of the present devices, apparatuses, kits, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the configurations described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the configurations depicted in the figures.

DESCRIPTION OF ILLUSTRATIVE EMBODIMENTS

Spinal Implant Device

Figure 9:
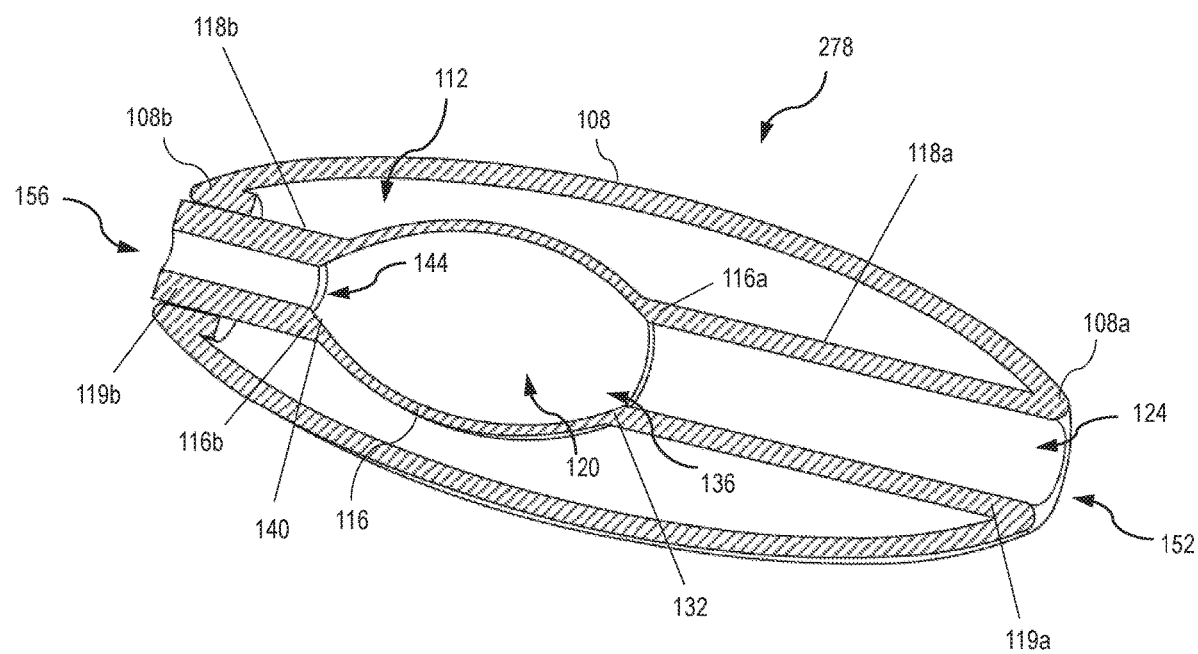
FIG. 9 shows a cross-sectional perspective view of the spinal device implant blank of FIG. 8 taken along a plane bisecting the spinal device implant blank after it has been partially inverted.

Referring now to the drawings, and more particularly to FIGS. 1-7, a spinal implant device 100 includes a flexible body 104 defining an outer fillable enclosure 108 defining an outer chamber 112 having a body aperture 114; an inner fillable enclosure 116 defining an inner chamber 120 such that the outer fillable enclosure 108 at least partially surrounds the inner fillable enclosure 116. The inner fillable enclosure 116 has an opening 124, as best shown in FIG. 9, in fluid communication with the inner chamber 120. A proximal plug 128 is configured to be coupled to the inner fillable enclosure 116 such that the proximal plug 128 controls fluid communication through the opening 124. In some configurations, the proximal plug 128 controls fluid communication through a re-sealable membrane 180 that can serve as a one-way valve and prevent any backflow of fluid from the inner chamber 120 into the outer chamber 112 when a fluid is delivered into the inner chamber 120. In this way, an inflation stylet 164, described in more detail below, can be configured to communicate with the inner chamber 120 and the outer chamber 112 through a single opening and without the contents of each chamber mixing together. Proximal plug 128 may be made of silicone or another material which is compatible with enclosures 108, 116, and may be manufactured using conventional manufacturing techniques, such as injection molding.

Figure 1:
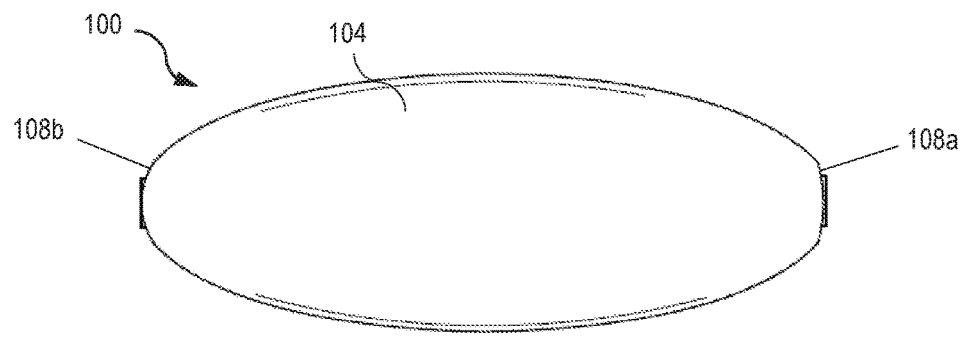
FIG. 1 shows a top view of an example of a configuration of a spinal implant device.
Figure 2:
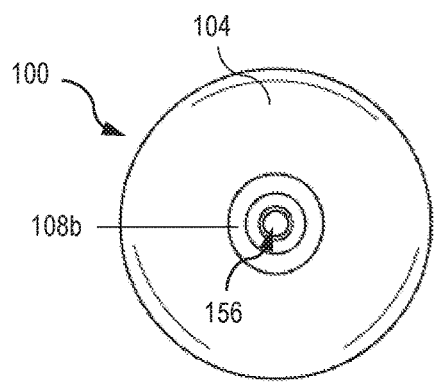
FIG. 2 shows a distal end view of the spinal implant device of FIG. 1.
Figure 3:
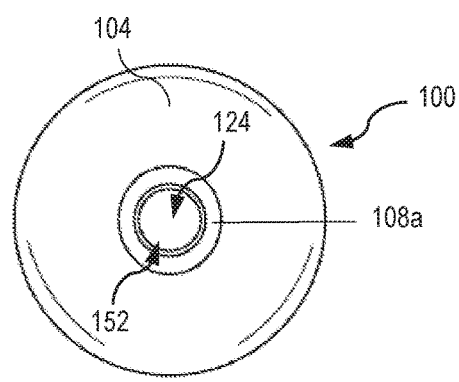
FIG. 3 shows a proximal end view of the spinal implant device of FIG. 1.
Figure 4:
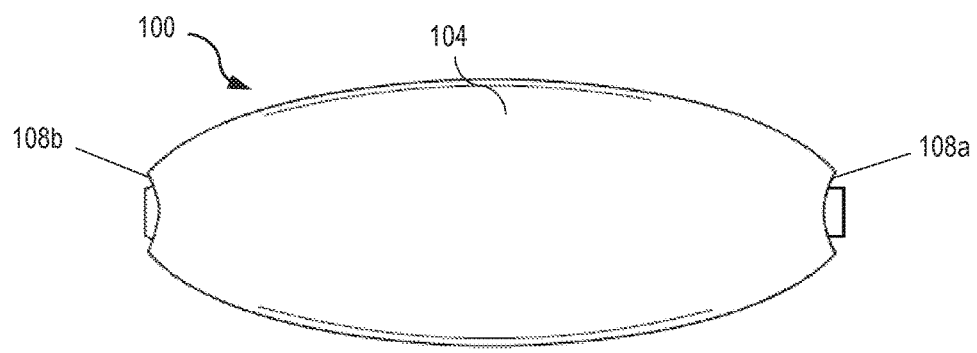
FIG. 4 shows a side view of the spinal implant device of FIG. 1.
Figure 5:
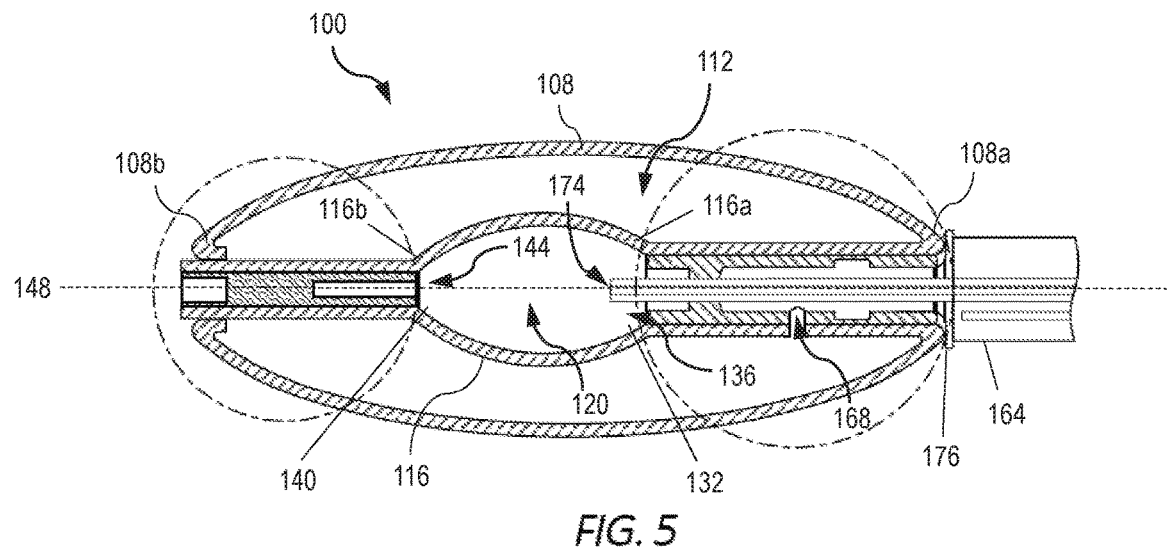
FIG. 5 shows a cut-away view of the spinal implant device of FIG. 1 with a distal plug and a proximal plug coupled to an inflation tip.
Figures 6, 7:
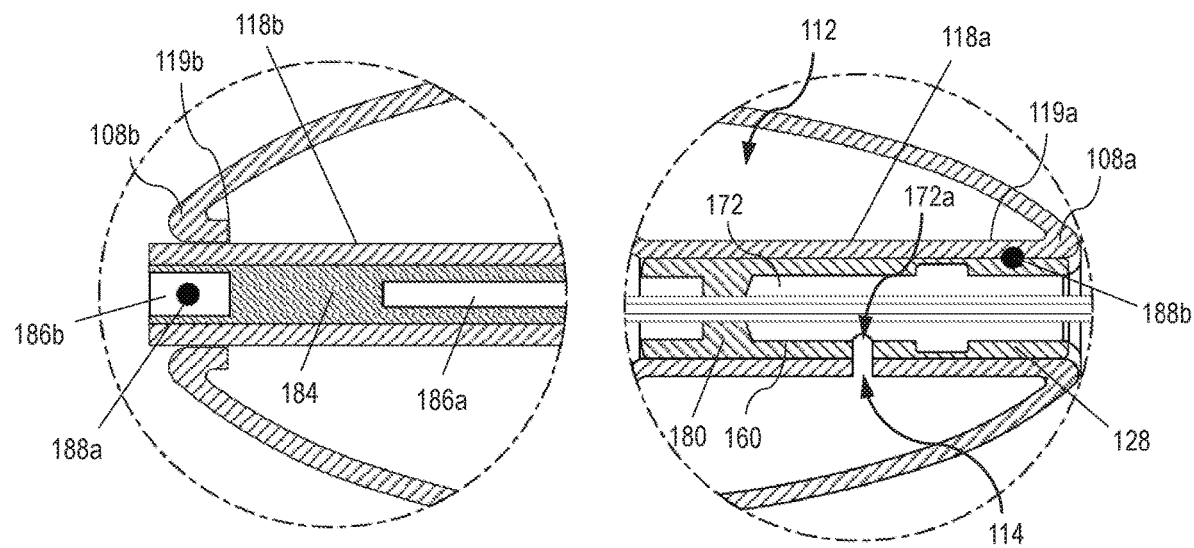
FIG. 6 shows an enlarged cut-away view of a configuration of the distal end of FIG. 5 with a radiopaque marker (e.g., tantalum marker bead) coupled to a distal plug.
FIG. 7 shows an enlarged cut-away view of the proximal end of FIG. 5 with a radiopaque marker (e.g., tantalum marker bead) coupled to a proximal plug.
Figure 8:
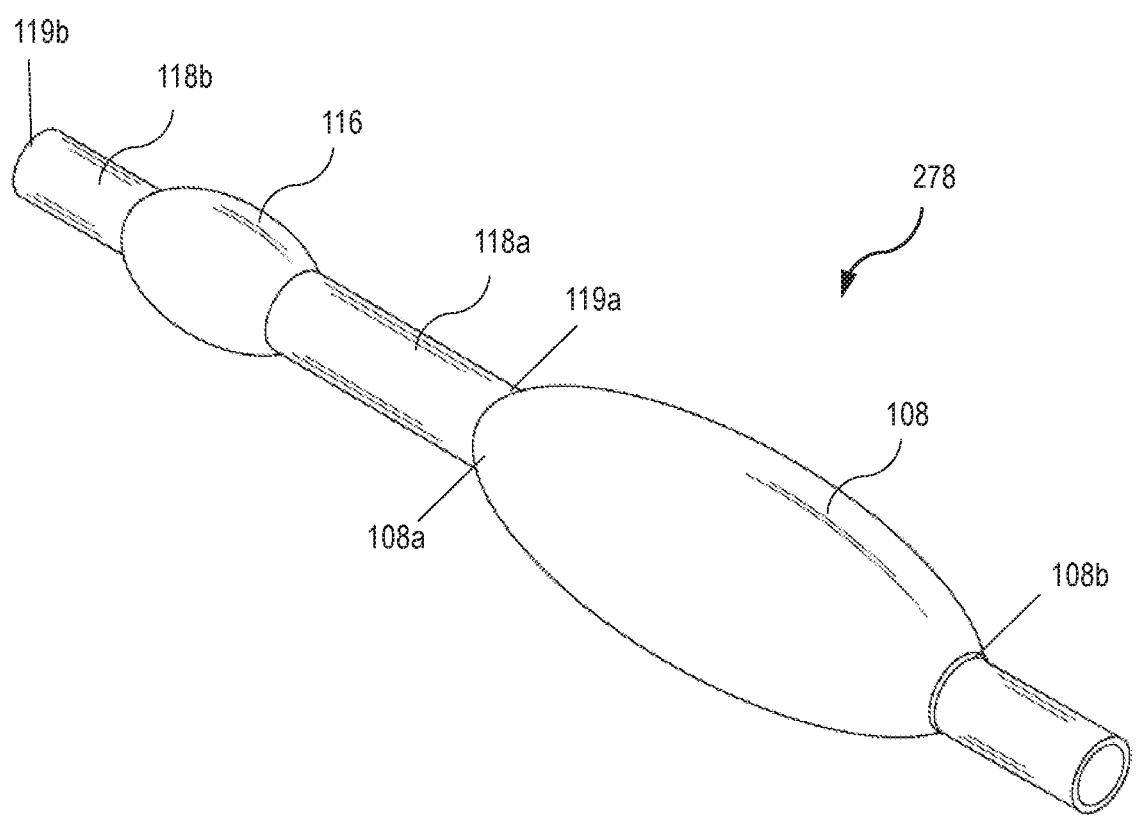
FIG. 8 shows a perspective view of a configuration of a spinal implant device blank for forming the spinal implant device of FIG. 1.

In some configurations, such as the one shown in FIGS. 5-7, outer fillable enclosure 108 has a first (or proximal) end 108a and a second (or distal) end 108b. Inner fillable enclosure 116 has a first (or proximal) end 116a coupled to a proximal neck 118a. A second (or distal) end 116b of inner fillable enclosure 116 is coupled to a distal neck 118b. An end portion 119a of proximal neck 118a is coupled to proximal end 108a of outer fillable enclosure 108, and an end portion 119b of distal neck 118b is coupled to distal end 108b of outer fillable enclosure 108. As best shown in FIG. 8, end portion 119a of proximal neck 118a is coupled to proximal end 108a of outer fillable enclosure 108 by forming them together as a unitary piece during the manufacturing process, as will be described in more detail below. Distal end 108b of outer fillable enclosure 108 is inverted and bonded to end portion 119b of distal neck 118b to form a substantially fluid tight seal. Coupling the enclosures together in this manner forms a substantially fluid tight outer chamber 112. Spinal implant device 100 is preferably sized so that it can be inserted using minimally invasive surgery techniques or percutaneously into an enucleated intervertebral disc cavity while deflated and then filled to fill the enucleated intervertebral disc cavity. In some configurations, the exterior of unfilled spinal implant device 100 is approximately 30 mm in length, 10 mm in width, and 10 mm in height, and the inner fillable enclosure 116 is approximately 8 mm long, 6 mm in diameter, and 0.3 mm thick. In some configurations, the wall thickness of the outer fillable enclosure 108 and inner fillable enclosure 116 may be formed to have varying wall thicknesses effective to achieve certain desired properties and/or functions. For example, the inner fillable enclosure 116 may have a wall thickness less than the outer fillable enclosure 108 to allow easier filling and expansion of the inner chamber 120 relative to the outer chamber 112. In some configurations, the inner chamber 120 can be configured to provide pressure feedback when the outer chamber 112 is filled, as will be described below. In some configurations, spinal implant device 100 can have a durometer between Shore 10A and Shore 100A. In this way, the spinal implant device 100, when combined with a curable medium described below, can exhibit an elastic modulus capable of dampening impacts or sudden increases in intra-discal pressure during bending, torsion, and/or other high loading peak movements. In at least this configuration, the spinal implant device 100 can further prevent spongeosus of adjacent bone and subsidence of the implant over time, thus mitigating migration and/or expulsion of the spinal implant device. In some configurations, the flexible body 104 includes a coating containing one or more ingredients selected from the list of ingredients consisting of:

drugs, bioactives, and/or stem cells. The flexible body 104 can also include a lubricious coating to aid in the delivery of the spinal implant device 100. Other ingredients may be chosen to achieve certain desired properties and/or functions. In this way, the spinal implant device 100 can further enhance repair and/or restoration of physiologic function of the intervertebral disc. In some configurations, the overall dimensions of unfilled spinal implant device 100 can be sized to be particularly suited for minimally invasive surgery, percutaneous surgery, robotic surgery, and/or robotics-assisted surgery. In some configurations, the outer chamber 112 does not expand significantly when it is filled (i.e., it is non-compliant or semi-compliant). In other configurations, the spinal implant device 100 is filled so that the spinal implant device 100 expands by approximately 100% (i.e., doubles in size) when implanted. In other configurations, the spinal implant device 100 is filled so that the spinal implant device 100 expands by more than 100% when implanted.

In some configurations, the outer and inner fillable enclosures 108, 116 comprise a unitary piece of material. In some configurations, such as the ones shown in FIGS. 1-7, the inner chamber 120 has a proximal end 132 with a proximal opening 136 and a distal end 140 with a distal opening 144. Although FIGS. 1-7 show a distal end 140 with a distal opening 144, other configurations of spinal implant device 100 may omit one or more features, such as a distal end 140 with a distal opening 144.

In some configurations, as best shown in FIG. 5, the outer fillable enclosure 108 and inner fillable enclosure 116 are axially symmetric around a longitudinal axis 148. In this way, the spinal implant device 100 will have a proper orientation in any direction when inserting the spinal implant device 100 into an enucleated intervertebral disc cavity. Further, the axially symmetric shape of the outer fillable enclosure 108 and inner fillable enclosure 116 allows the spinal implant device 100 to expand, when combined with a curable medium (e.g., curable silicone containing 12% barium sulfate), circumferentially around the longitudinal axis 148 to fill the entire enucleated space by accounting for the expansion behavior of the curable medium.

The flexible body 104 may further define a proximal opening 152 in fluid communication with the inner chamber 120. The flexible body 104 may further define a distal opening 156 in fluid communication with the inner chamber 120. A proximal plug 128 defines a receptacle 160 configured to receive a portion of an inflation stylet 164 for delivering a fluid to the inner chamber 120 and outer chamber 112. A plug aperture 168 is in fluid communication with the outer chamber 112 when aligned with the body aperture 114. Proximal neck 118a may have features, such as grooves, for mating with matching features on proximal plug 128 to assist in locating proximal plug 128. Proximal plug 128 may be inserted into and bonded with proximal neck 118a. Proximal plug 128 can be configured to be coupled to an inflation tip 172 of an inflation stylet 164. In some configurations, the receptacle 160 has a diameter between 1.0 mm and 1.5 mm at a widest diameter, a diameter between 0.8 mm and 1.2 mm at a narrowest diameter, and a length between 7.0 mm and 8.0 mm. In some configurations, proximal plug 128 has a length between 9.5 mm and 10.0 mm and an outside diameter between 2.0 mm and 2.5 mm.

Figure 10:
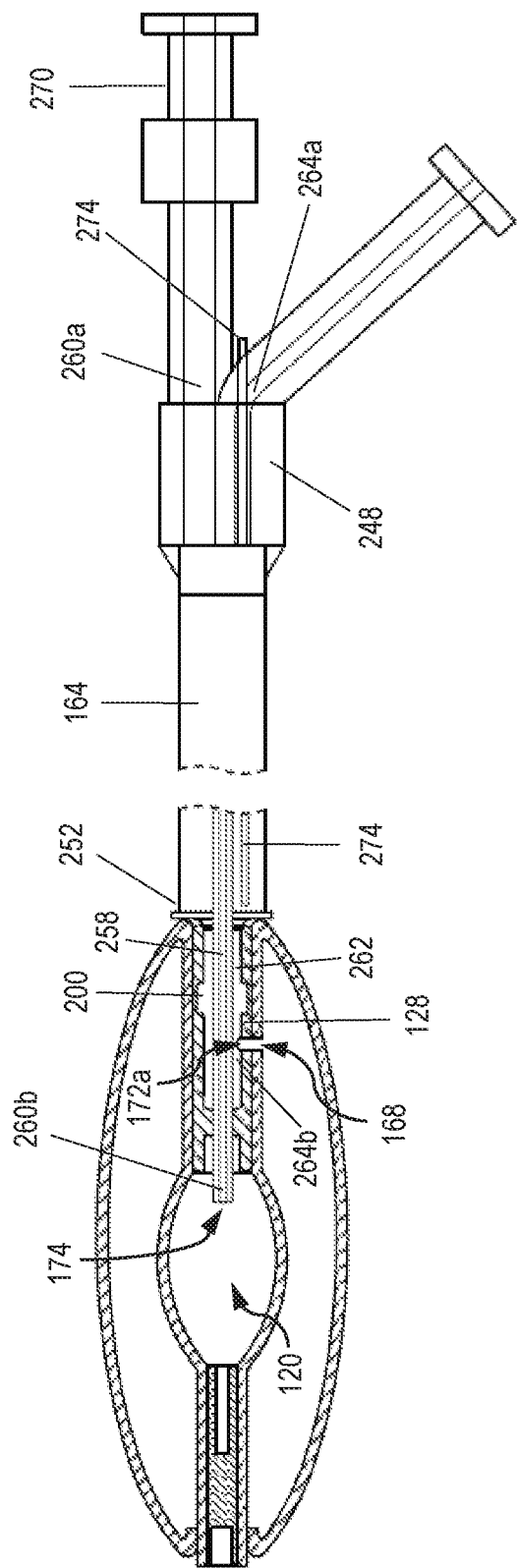
FIG. 10 shows a cut-away view of the spinal implant device of FIG. 5 coupled to a configuration of an inflation stylet.

In some configurations, the inflation stylet 164 includes an inflation tip 172 for delivering the fluid to the outer chamber 112, the inflation tip 172 configured to be coupled to a distal end 252 of the inflation stylet 164. Although FIG. 10 shows inflation stylet 164 coupled to an inflation tip 172, some configurations of the inflation stylet 164 may omit one or more features, such as the inflation tip 172, and still achieve similar functions. For example, distal end 176 of inflation stylet 164 can be configured to be coupled to the proximal plug 128.

In some configurations, the proximal plug 128 includes a re-sealable membrane 180 to control fluid communication through the proximal opening 136 of the inner chamber 120. In some configurations, the re-sealable membrane 180 has a thickness of between 0.6 mm and 1.0 mm.

In this way, the re-sealable membrane prevents fluid from flowing around the first (contrast) lumen 258 and into the outer chamber 112. The re-sealable membrane 180 can also serve as a one-way valve and prevent any backflow of fluid from the inner chamber 120 into the outer chamber 112 when a fluid is delivered into the inner chamber 120. In this way, an inflation stylet 164, described in more detail below, can be configured to communicate with the inner chamber 120 and the outer chamber 112 through a single opening and without the contents of each chamber mixing together.

In some configurations, as shown in FIG. 5, the spinal implant device 100 further includes a distal plug 184 disposed in distal neck 118b to seal the distal opening 144. Distal plug 184 may define a proximal cylindrical recess 186a at a proximal end of distal plug 184 for receiving a distal end 260b of the first (contrast) lumen 258 of inflation stylet 164, and a distal cylindrical recess 186b at a distal end of distal plug 184. Distal plug 184 may be made of silicone or another material that is compatible with enclosures 108, 116, and may be manufactured using conventional manufacturing techniques, such as injection molding. In some configurations, distal plug 184 has an outside diameter between 1.0 mm and 1.3 mm, and a length between 7.8 mm and 8.2 mm. In some configurations, the proximal cylindrical recess 186a has a diameter between 0.4 mm and 0.8 mm, and a length between 3.3 mm and 3.8 mm. In some configurations, the distal cylindrical recess 186b has a diameter between 0.6 mm and 1.0 mm, and a length between 1.3 mm and 1.8 mm. Although FIGS. 5-6 show a distal plug 184, one or more configurations of spinal implant device 100 may omit one or more features, such as the distal plug 184.

In some configurations, such as the one shown in FIG. 6, the spinal implant device 100 further includes a first radiopaque marker (e.g., tantalum marker bead) 188a coupled to either the distal plug 184 or a portion of the flexible body 104 that is closer to the distal opening 144 of the inner chamber 120 than to the proximal opening 136 of the inner chamber 120. Although FIG. 6 shows a first radiopaque marker 188a, one or more configurations of spinal implant device 100 (e.g., FIG. 5) may omit one or more features, such as the first radiopaque marker 188a.

In some configurations, such as the one shown in FIG. 7, the spinal implant device 100 further includes a second radiopaque marker (e.g., tantalum marker bead) 188b coupled to either the proximal plug 128 or a portion of the flexible body 104 that is closer to the proximal opening 136 of the inner chamber 120 than to the distal opening 144 of the inner chamber 120. Although FIG. 7 shows a second radiopaque marker 188b, one or more configurations of spinal implant device 100 (e.g., FIG. 5) may omit one or more features, such as the second radiopaque marker 188b.

In some configurations, the outer chamber 112 is filled with a curable medium 224 (e.g., curable silicone material). In some configurations, the curable medium 224 contains a radiographic material 196 (identified as the black dots within outer chamber 112 in FIGS. 16D-16F). In some configurations, the radiographic material 196 contains 8 to 16 wt. % of barium sulfate. In some configurations, the curable medium 224 substantially cures within ten minutes. In some configurations, the curable medium 224 is substantially de-gassed prior to delivery into the outer chamber 112. In some configurations, a retaining element 200 for retaining the spinal implant device 100 on the inflation stylet 164 is provided.

Inflation Stylet and Delivery Sheath

Figure 11:
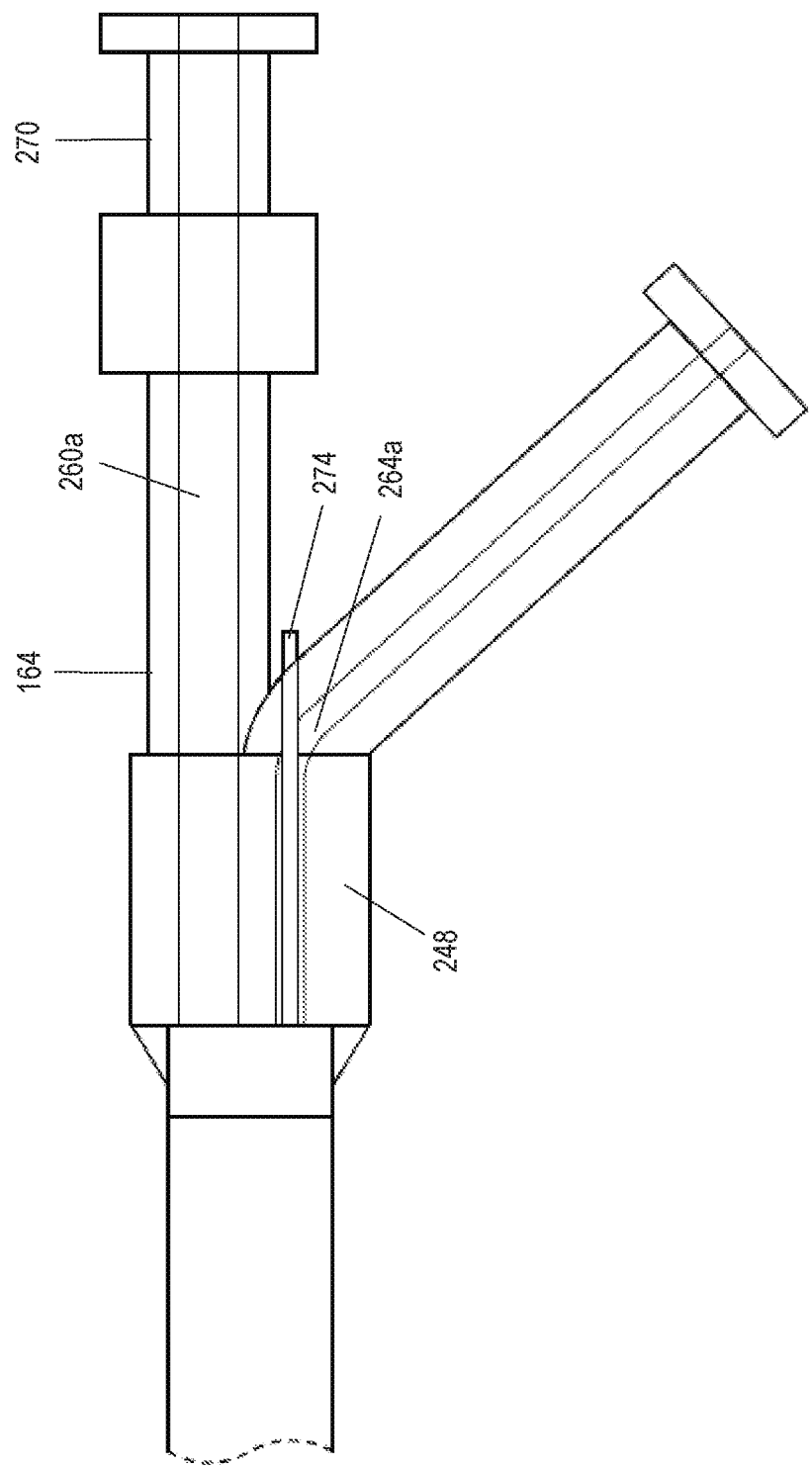
FIG. 11 shows a side plan view of the proximal end of the inflation stylet of FIG. 10.
Figure 12:
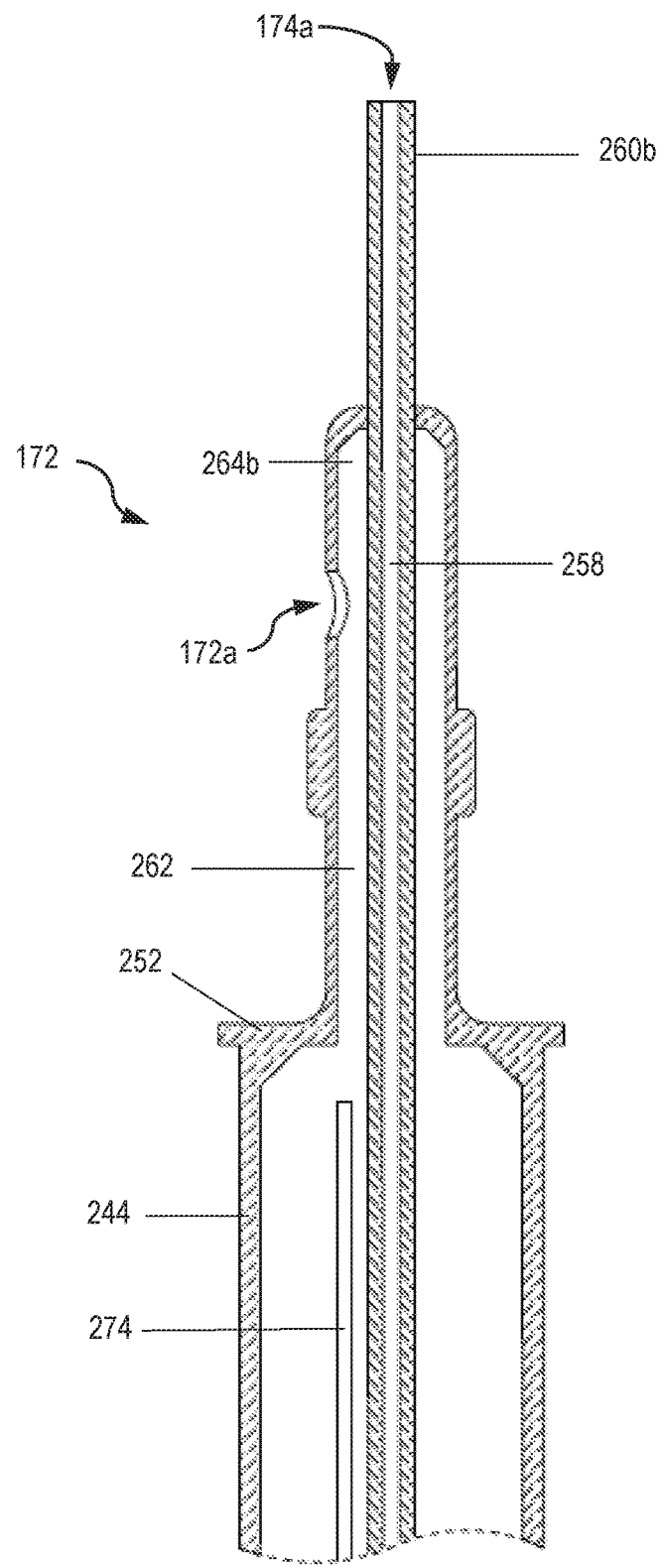
FIG. 12 shows a cross-sectional side view of a configuration of an inflation tip.

Referring now to FIGS. 10-13, in some configurations inflation stylet 164 may be used in conjunction with a delivery sheath 240 to deliver and deploy spinal implant device 100. Inflation stylet 164 includes a shaft 244 with a proximal end 248 and a distal end 252. A first (contrast) lumen 258 and a second (silicone) lumen 262 extend through shaft 244. The distal ends of first and second lumens 258, 262 can be coupled to an inflation tip 172 that can be configured to mate with proximal plug 128. For example, as shown in FIGS. 5, 10, and 12, the inflation tip 172 can be configured to include a retaining element 200 (e.g., key or groove) that can aid in physically preventing improper installation of inflation stylet 164. In this way, retaining element 200 may be used to control the insertion depth of inflation tip 172. In some embodiments, retaining element 200 can be used as a locking feature to help prevent inadvertent dislodgment of inflation stylet 164 from proximal plug 128. For example, as best shown in FIG. 7, proximal plug 128 may be configured with receptacle 160 adapted to mate with retaining element 200 on inflation tip 172 such that inflation tip is prevented from dislodging out of the proximal plug 128 prior to deployment. In some configurations, retaining element 200 can have a diameter between 1.8 mm and 2.2 mm at a widest point.

In some configurations, inflation tip 172 comprises stainless steel (e.g., 304 stainless steel). In some configurations, inflation tip 172 defines a proximal tip opening 174 that aligns with first (contrast) lumen 258 when coupled to distal end 252 of inflation stylet 164. In some configurations, proximal tip opening 174 has a diameter between 0.51 mm to 0.6 mm.

Referring now to FIGS. 10 and 12, first (contrast) lumen 258 extends from proximal end 248 of inflation stylet 164 to distal end 252 of inflation tip 172. First (contrast) lumen 258 extends out the proximal end of inflation stylet 164. In some configurations, first (contrast) lumen 258 can be independently movable with respect to inflation stylet 164 so that the position of the distal end 260*b* of first (contrast) lumen 258 may be extended and withdrawn with respect to the distal end 252 of inflation stylet 164. For delivery prior to implantation, first (contrast) lumen 258 can extend through re-sealable membrane 180 and the distal end 260*b* of first (contrast) lumen 258 can be positioned within the inner chamber 120 to deliver fluidic medium 220 (e.g., contrast medium). First (contrast) lumen 258 can be used to both deliver and remove fluids from inner chamber 120. In some configurations, distal end 260*b* of first (contrast) lumen 258 can be pre-formed using shape memory material into a shape that allows easier delivery and/or removal of fluid from inner chamber 120. For example, in one specific configuration, first (contrast) lumen 258 can be pre-formed into a curved shape that allows easier access to the bottom (or top) of inner chamber 120. The curved shape, combined with the ability to extend and withdraw first (contrast) lumen 258 allows it to be adjusted when used to withdraw fluid from inner chamber 120. It should be understood that as used herein, "first (contrast) lumen" should be understood to mean a lumen for delivery of any desired fluid to inner chamber 120, and can encompass materials other than contrast medium. Contrast medium may be used to ensure visibility under imaging, such as fluoroscopy.

As best shown in FIG. 7, when inflation stylet 164 is mated with proximal plug 128, the inflation tip aperture 172*a* is in fluid communication with the distal end 264*b* of second (silicone) lumen 262 and coincident with plug aperture 168 of proximal plug 128 to allow fluid communication between the outer chamber 112 and second (silicone) lumen 262 through the body aperture 114 of outer chamber 112. When inflation tip 172 is coupled to distal end 252 of inflation stylet 164, curable silicone material 192 can be delivered through inflation tip aperture 172*a* when plug aperture 168 and body aperture 114 are aligned. In some configurations, inflation tip aperture 172*a* has a diameter between 0.7 mm and 1.0 mm. Proximal end 260*a* of first (contrast) lumen 258 and proximal end 264*a* of second (silicone) lumen is provided with a connector 270 (e.g., luer connector) for connection to common inflation tools (e.g., syringes) known to those of skill in the art.

In some configurations, as best shown in FIGS. 10-12, inflation stylet 164 further includes a vent lumen 274 in fluid communication with the second (silicone) lumen 262. In this way, vent lumen 274 may be provided to allow air to exit second (silicone) lumen 262 when silicone or another suitable material is delivered to outer chamber 112. Vent lumen 262 may be configured to be large enough to allow air to freely move through it, while resisting more viscous fluids such as curable silicone (e.g., 192). In some configurations, the curable silicone material 192 is substantially de-gassed prior to delivery into the outer chamber 112. It should be understood that as used herein, "second (silicone) lumen" means a lumen for delivery of any desired fluid to outer chamber 112, and can encompass materials other than silicone or curable silicone, including, but not limited to, curable silicone blends containing barium sulfate. Vent lumen 274 preferably extends through shaft 244 to vent to atmosphere at the proximal end 248 of inflation stylet 164.

Figure 13:
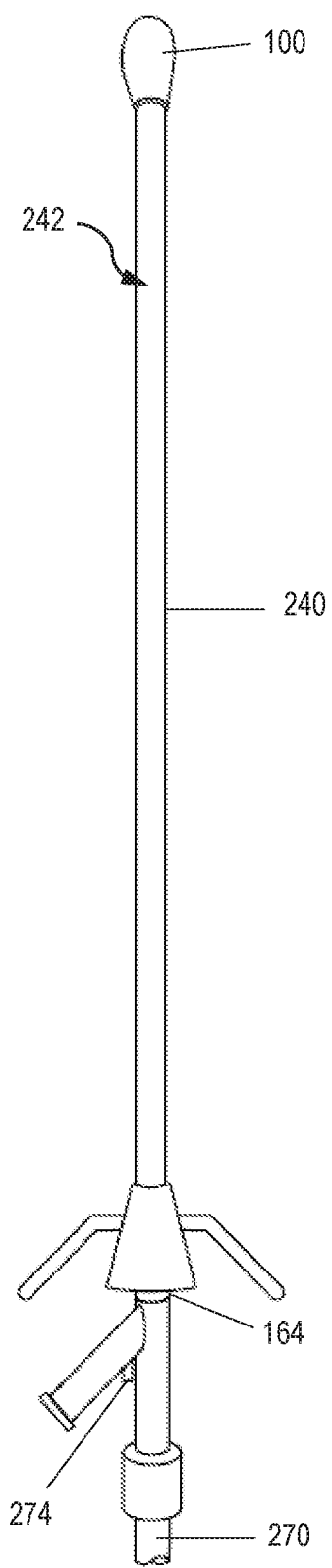
FIG. 13 shows the inflation stylet of FIG. 10 with a delivery sheath deploying a configuration of a spinal implant device.

Referring now to FIG. 13, a delivery sheath 240 includes a lumen 242 sized to fit over shaft 244 of inflation stylet 164. To deliver spinal implant device 100, the spinal implant device 100 is coupled to inflation tip 172, and the assembled bodies are withdrawn into the distal end of delivery sheath 240.

Method of Manufacturing a Spinal Implant Device

Referring to FIGS. 8 and 9, spinal implant device 100 may be formed by forming an elastomeric spinal implant blank 278, which comprises outer fillable enclosure 108 coupled to inner fillable enclosure 116. Spinal implant blank 278 may be manufactured using conventional manufacturing techniques, such as, but not limited to, injection molding or dip molding. In some implementations, a multi-piece mandrel can be used to form the spinal implant blank 278. In some implementations, the wall thickness of the outer fillable enclosure 108 and inner fillable enclosure 116 may be formed using the multi-piece mandrel to have varying wall thicknesses effective to achieve certain desired properties and/or functions. The multi-piece mandrel may be configured to have varying thicknesses and geometries to achieve the desired properties and/or functions for the spinal implant device 100. For example, the inner fillable enclosure 116 may be formed to have a wall thickness less than the outer fillable enclosure 108 to allow easier filling and expansion of the inner chamber 120 relative to the outer chamber 112. After spinal implant blank 278 is formed, spinal implant blank 278 is partially inverted, as shown in FIG. 9, to place inner fillable enclosure 116 into the interior of outer fillable enclosure 108. Distal plug 184 can then be inserted into distal neck 118*b*, and proximal plug 128 can then be inserted into proximal neck 118*a*. Inflation tip 172 can then be coupled to the proximal plug 128 and a guidewire inserted into inflation tip 172 and extending through inflation tip aperture 172*a* to pierce an opening to form body aperture 114. In some configurations, spinal implant blank 278 includes a proximal neck 118*a* having a diameter between 3.0 mm and 4.0 mm; a distal neck 118*b* having a diameter between 2.0 mm and 2.9 mm; an inner fillable enclosure having a diameter of between 5.0 mm and 6.0 mm at a widest diameter around a longitudinal axis 148; and an outer fillable enclosure having a diameter between 22.0 mm and 26.0 mm at a widest diameter around the longitudinal axis 148. In some configurations, spinal implant blank 278 has a total length between 52.0 mm and 60.0 mm. In some configurations, the thickness of the outer wall of proximal neck 118*a* is between 0.3 mm and 0.7 mm. In some configurations, the thickness of the outer wall of distal neck 118*b* is between 0.6 mm and 1.0 mm.

Additional details regarding one example of a manufacturing technique are disclosed in application 62/074,295, entitled "Percutaneous Implantable Nuclear Prosthesis," which was filed on Nov. 4, 2014 and is hereby incorporated by reference in its entirety. In some implementations of the method of manufacturing, the spinal implant blank 278 may be stripped from the mandrel by separating the multi-piece mandrel to prevent tearing of the spinal implant blank 278 as the blank is removed from the mandrel.

Method of Deploying a Spinal Implant Device

Referring now to FIGS. 14A-16F, in some implementations, a method of replacing a nucleus pulposus 204 of an intervertebral disc 208 with a spinal implant device (e.g., 100) comprises dilating the annulus fibrosus 212 to gain access to an intervertebral disc 208 while leaving annulus fibrosus 202 substantially intact. Preferably, accessing the intervertebral disc 208 is performed using minimally invasive surgical techniques, such as percutaneous techniques, which uses an access cannula 280 to access the intervertebral disc cavity 216 through a small opening in annulus fibrosus 212. In some implementations, the intervertebral disc cavity 216 is accessed using a posterolateral approach through Kambin's triangle using a lateral transpsoas open surgical approach to the L5-S1 lumbar spinal disc nucleus pulposus 204. In some implementations, an anterior approach may also be used. In some implementations, the intervertebral disc cavity 216 is access using a lateral transpsoas open surgical approach to the L1-L5 lumbar spinal disc nucleus pulposus 204 (when anatomy permits), and a retroperitoneal (i.e., anterolateral) open surgical approach to the L5-S1 lumbar spinal disc nucleus pulposus 204.

Figure 14A:
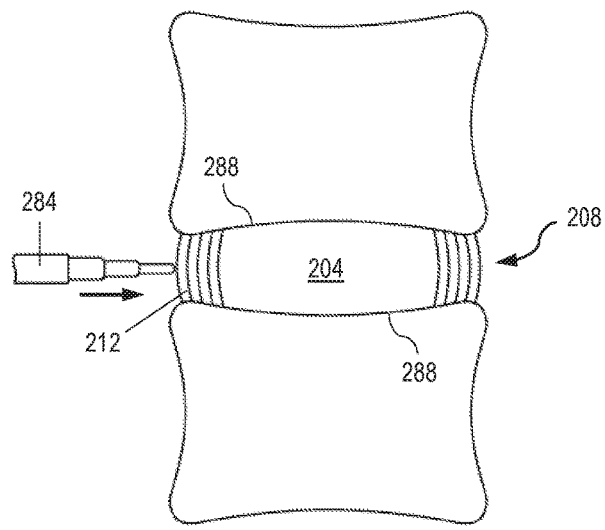
FIG. 14A shows a first step in dilating the annulus fibrosus using a dilator with a first diameter to gain access to an intervertebral disc.
Figure 14B:
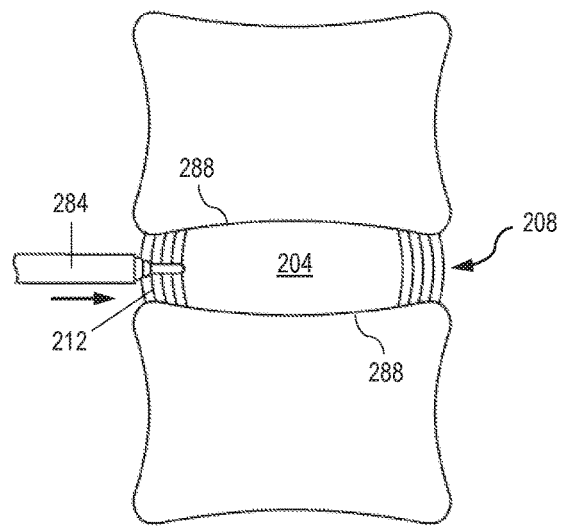
FIG. 14B shows a second step in dilating the annulus fibrosus with the dilator of FIG. 15A using a second diameter to gain access to an intervertebral disc.
Figure 14C:
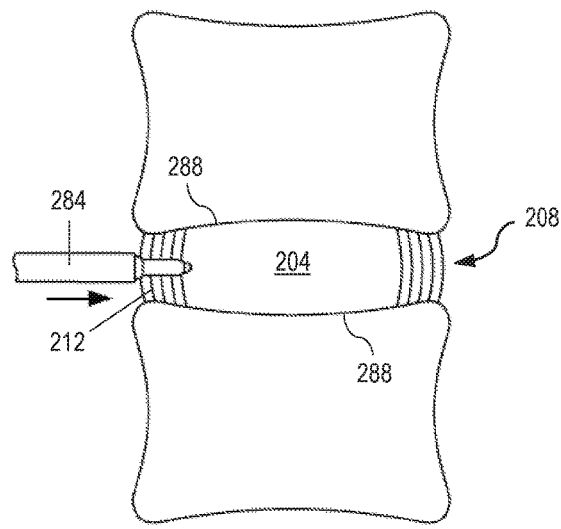
FIG. 14C shows a third step in dilating the annulus fibrosus with the dilator of FIG. 15A using a third diameter to gain access to an intervertebral disc.
Figure 14D:
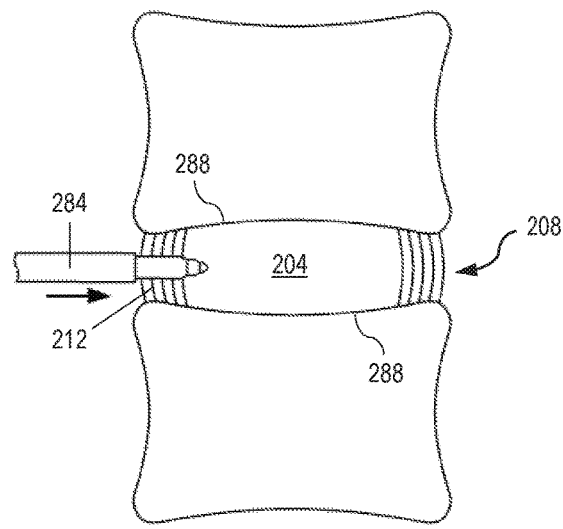
FIG. 14D shows a fourth step in dilating the annulus fibrosus with the dilator of FIG. 15A using a fourth diameter to gain access to an intervertebral disc.

As best shown in FIGS. 14A-14D, to preserve the integrity of the annulus fibrosus 212 as much as possible, access through the annulus fibrosus 212 may be created by controlled dilation of the annulus fibrosus 212 by inserting a guide pin (e.g., a K-wire) and then a series of increasing diameter dilators 284 placed over the guide pin (not shown). Once the desired diameter is obtained, the access cannula 280 is placed over the largest diameter dilator 284, and the dilator set 284 is removed. In some configurations, the intervertebral disc access system can include a first dilator having an outside diameter of about 2 mm; a second dilator having an outside diameter of about 3.5 mm; a third dilator having an outside diameter of about 5 mm; and, a fourth dilator having an outside diameter of about 6 mm. In some configurations, the disc access system can include dilators sized to be particularly suited for a surgical technique (e.g., minimally invasive surgery, percutaneous surgery, robotic surgery, and/or robotics-assisted surgery). The tip of the first dilator is placed on the midpoint of the craniocaudal dimension of the annulus fibrosus 212. Fluoroscopy can be used to ensure good position of the dilator (e.g., when access starts at the midpoint of the craniocaudal dimension of the intervertebral disc margin, parallel to the vertebral end plates 288 and with a trajectory that will facilitate total nucleus pulposus 204 removal). Dilation of the annulus fibrosus 212 is then started by advancing the first dilator, as shown in FIG. 14A, with a gentle rotation of the dilator, and confirmation of position can be obtained with fluoroscopy. The second, third, and fourth dilators can be advanced similarly (FIGS. 14B, 14C, 14D, respectively) and confirmed under fluoroscopy to ensure that the dilators 284 are not advanced beyond the margin of the inner annulus fibrosus 212 opposite the access site. Once the largest dilator is in place, the dilators 284 may be removed in its entirety to allow for the passage of conventional surgical instruments (e.g., rongeurs) for removal of the nucleus pulposus 204. To ensure safety of subsequent steps, access cannula 280 may be advanced over the largest dilator prior to dilator removal to secure the access into the intervertebral disc cavity 216. Access cannula 280 should not be placed further than the midline of the intervertebral disc space. This procedure gradually spreads the fibrous bands of the annulus fibrosus 212 to create access to the nucleus pulposus 204 without excising (i.e., removing, tearing, or otherwise harming) any tissue, which aids in the healing process and successful deployment of the implantable nuclear prosthesis.

Once the nucleus pulposus 204 is reached, a nuclectomy is then performed with any suitable surgical instrument (e.g., rongeurs) to create an enucleated intervertebral disc cavity 216. Once the existing nucleus pulposus 204 has been removed to the satisfaction of the physician, annulus fibrosus 212 and vertebral end plates 288 form a substantially empty enucleated intervertebral disc cavity 216 as shown in FIG. 16A.

Figure 16A:
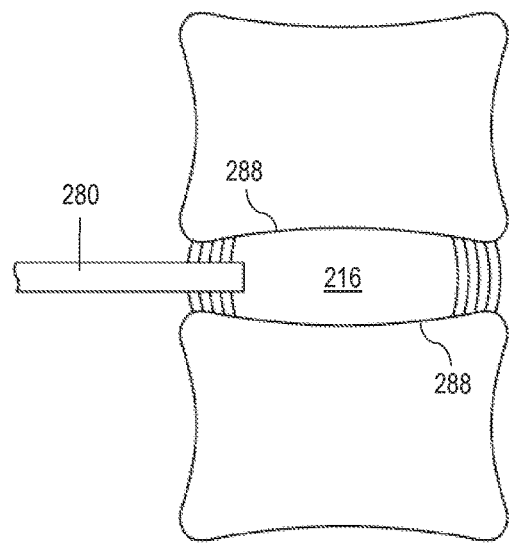
FIG. 16A shows a first step in implanting the spinal implant device of FIG. 5 through an access cannula positioned in the enucleated disc cavity.
Figure 16B:
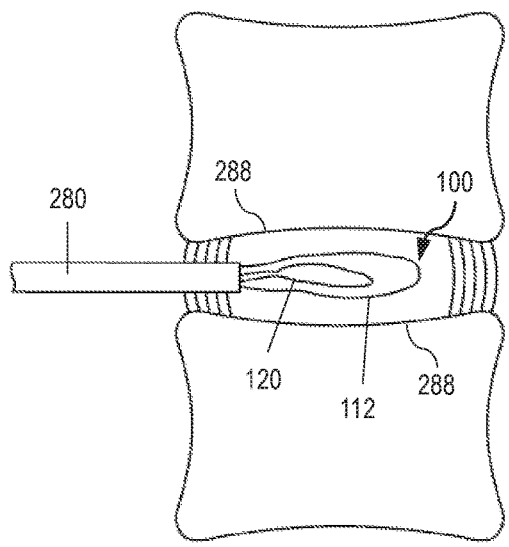
FIG. 16B shows a second step in implanting the spinal implant device of FIG. 5 by inserting the spinal implant device through the access cannula of FIG. 16A into the enucleated disc space.

Referring now to FIGS. 16A-16F, any one of the configurations of present spinal implant devices (e.g., 100), including configurations of a dual-chambered spinal implant device, can then be inserted into the enucleated intervertebral disc cavity 216. The dual-chambered spinal implant device can have an inner chamber that is at least partially surrounded by an outer chamber, and configured such that the inner chamber provides pressure feedback when the outer chamber is filled. The spinal implant device 100, which is loaded into a delivery sheath 240, is placed into enucleated disc cavity 216 through access cannula 280, as shown in FIGS. 16A-16B. Typically, the spinal implant device 100 will be delivered to the far end of the enucleated intervertebral disc cavity 216. The delivery sheath 240 is then withdrawn to expose the spinal implant device 100 inside the enucleated intervertebral disc cavity 216.

Figure 16C:
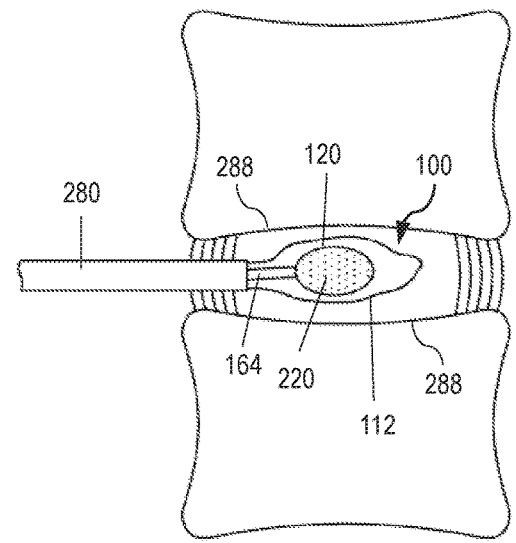
FIG. 16C shows a third step in implanting the spinal implant device of FIG. 5 by inflating the inner chamber with a fluidic medium (e.g., contrast medium).

As shown in FIGS. 16B-16C, the inflation stylet 164 is then used to fill the inner chamber 120 with a fluidic medium 220 (e.g., contrast medium). Inner chamber 120 can be filled with a threshold volume (e.g., 0.25 mL of contrast medium), or until the inner chamber 120 reaches a threshold volume sufficient to provide pressure feedback. In some implementations, a substantially incompressible fluid is used, such as a contrast medium. Prior to inflating the inner chamber 120, air should be purged from the system using, for example, a vacuum locking syringe. Fluidic medium 220 (e.g., contrast medium) is then delivered through first (contrast) lumen 258 of inflation stylet 164. In some implementations, the inner chamber 120 is filled with contrast medium to a threshold volume between 0.2 mL to 0.3 mL.

Figure 16D:
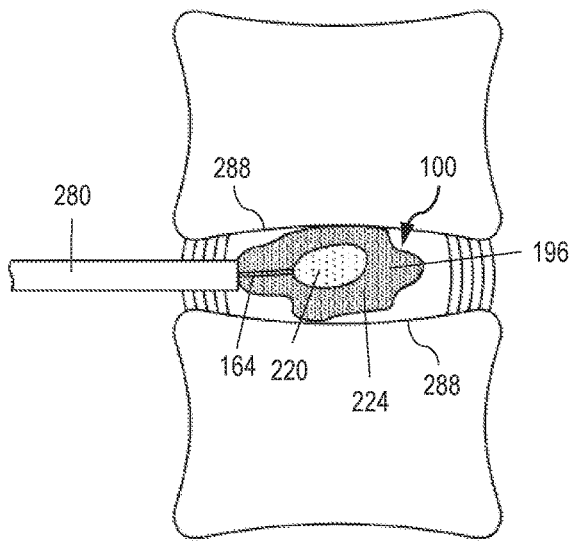
FIG. 16D shows a fourth step in implanting the spinal implant device of FIG. 5 by inflating the outer chamber with a curable radiopaque medium.

As shown in FIG. 16D, inflation stylet 164 is then used to deliver a curable medium 224 to outer chamber 112, thereby inflating the outer chamber 112 to a threshold pressure (e.g., 40 psi). The pressure applied from the outer chamber 112 to the inner chamber 120 during delivery of the curable medium 224 is monitored as pressure feedback to ensure the threshold pressure is not exceeded. Curable medium 224 is preferably an elastomeric material, such as silicone rubber containing a radiopaque material (e.g., barium sulfate). In some implementations, the curable medium 224 contains silicone and an effective amount of a radiopaque material making the curable medium 224 radiopaque and having a viscosity that permits flow into the outer chamber. In some implementations, the curable medium 224 contains silicone and 8 to 16 wt. % of barium sulfate. In some implementations, delivery of curable medium 224 to outer chamber 112 is performed under continuous fluoroscopic control and delivered slowly to permit intermittent verification of the exit of the curable medium 224 into the outer chamber 112, monitoring of delivery pressure to ensure delivery pressure does not exceed a threshold pressure (e.g., 40 psi), monitoring of distribution of curable medium 224 and checking for any possible extra-discal diffusion. In some implementations, the threshold pressure can be between 35 psi to 45 psi. Inflation pressure can be monitored with a pressure monitoring device such as, for example, the QL® inflation device (ATRION® Medical). In some implementations, it is not necessary to evacuate air from the outer chamber 112 because of the presence of the vent lumen 274. Curable medium 224 may be chosen so that it polymerizes with the material of outer and inner fillable enclosures 108, 116 to form a unitary member. The modulus of elasticity and other characteristics of curable medium 224 can be selected based upon patient specific parameters. For example, younger, more active patients may require a firmer material than less mobile geriatric patients.

Figure 16E:
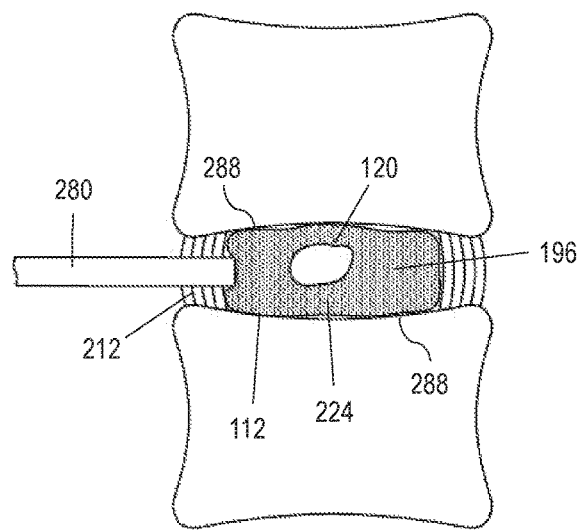
FIG. 16E shows a fifth step in implanting the spinal implant device of FIG. 5 by removing the fluidic medium (e.g., contrast medium) from the inner chamber after the curable radiopaque medium has inflated the outer chamber.

As shown in FIG. 16E, once outer chamber 112 is filled to a threshold pressure, curable medium 224 is allowed to cure. In some implementations, the curable medium 224 contains curable silicone which substantially cures in a short period of time, for example, about 10 minutes or less. The use of shorter curing periods may help prevent the dissolution of solvent from the curable medium 224 to the fillable enclosures which may occur with longer curing mediums. Such leaching of solvents may adversely affect the structural integrity of the fillable enclosures.

After curable medium 224 is allowed to cure, the fluidic medium 220 (e.g., contrast medium) from the inner chamber 120 is removed using first (contrast) lumen 258. As previously discussed, first (contrast) lumen 258 may be moved and/or manipulated to remove as much contrast medium as is desired. Preferably, substantially all of the contrast medium is removed; however, some contrast medium will likely remain and it is not necessary to remove all of the contrast medium. In some configurations, the inner fillable enclosure 116 is then left vented so that fluids may enter and exit the inner fillable enclosure 116. Once contrast medium has been removed and curable medium 224 is sufficiently cured, inflation stylet 164 can be rotated up to 360 degrees to de-couple the spinal implant device 100 from the inflation stylet 164. The inflation stylet 164 can then be withdrawn through access cannula 280, and access cannula 280 can subsequently be removed.

Figure 16F:
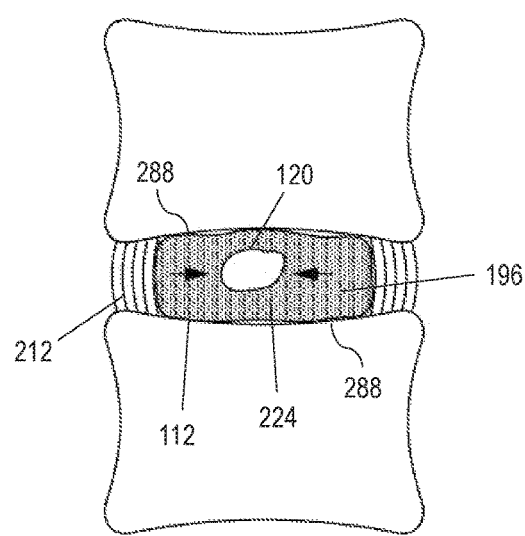
FIG. 16F shows a sixth step in implanting the spinal implant device of FIG. 5 with the fibers of the annulus fibrosus realigned to preserve annulus fibrosus integrity, the outer chamber cured with radiopaque material, and horizontal load stresses directed inward toward the hollow inner chamber.

As shown in FIG. 16F, in the implanted state, the spinal implant device 100 comprises an annular ring of cured material 224 surrounding hollow inner chamber 120. This structure allows for vertical and horizontal load stresses placed on the intervertebral disc space to be redirected inward, centrally toward inner chamber 120 (see direction arrows of FIG. 16F) instead of outward. Moreover, the expansion ability of spinal implant device 100 as the outer chamber 112 is filled allows spinal implant device 100 to effectively bridge any defects in the annulus fibrosus 212. Upon removal of access cannula 280, the fibers of the annulus fibrosus 212 realign to preserve annulus fibrosus integrity.

Figure 15A:
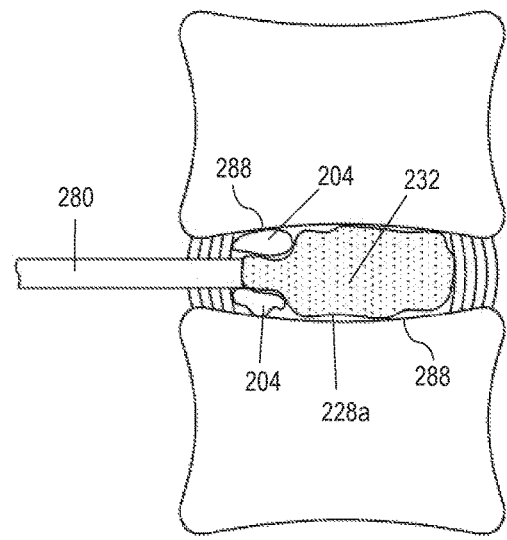
FIG. 15A shows a configuration of a present imaging balloon inflated with a radiopaque fluid to assess the completeness of a nuclectomy.

In some implementations, as shown in FIG. 15A, after performing the nuclectomy, an imaging balloon (e.g., a first imaging balloon 228a) is inserted into the enucleated intervertebral disc cavity 216 and inflated with a radiopaque fluid 232 to assess completeness of the nuclectomy. The nuclectomy is repeated as needed to remove any remaining nucleus pulposus 204. The inflating and nuclectomy steps are repeated until the enucleated intervertebral disc cavity 216 has been sufficiently enucleated. In some implementations, first imaging balloon 228a can include an inflatable elastomeric material having a durometer of between Shore 10A to Shore 100A (e.g., Shore 20A). First imaging balloon 228a can be inserted into access cannula 280 and advanced to position the first imaging balloon 228a within the enucleated intervertebral disc cavity 216. Radiopaque fluid 232 (e.g., contrast medium) can be delivered through the first (contrast) lumen 258 to inflate first imaging balloon 228a to a threshold pressure (e.g., 30 psi). In some implementations, the threshold pressure is not to exceed 30 psi for repeated imaging to assess the nuclectomy. Inflation pressure can be monitored with a pressure monitoring device such as, for example, the QL® inflation device (ATRION® Medical). Assessment of the completeness of the nuclectomy can then be performed under fluoroscopic guidance and repeated until a satisfactory total nucleus removal has been accomplished.

Figure 15B:
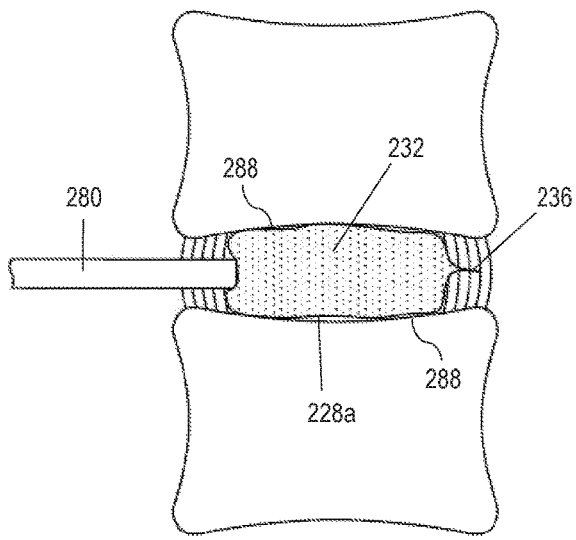
FIG. 15B shows a configuration of a present imaging balloon inflated with a radiopaque fluid to interrogate the annulus fibrosus for a defect (e.g., tear, herniation).
Figure 15C:
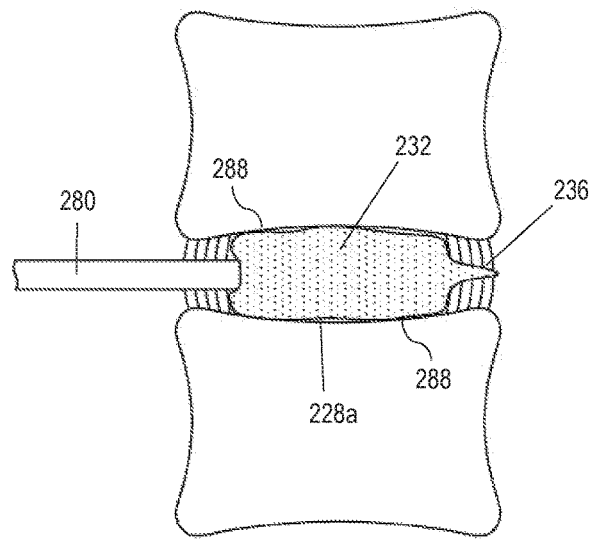
FIG. 15C shows a configuration of a present imaging balloon inflated with a radiopaque fluid identifying and extending through a defect in the annulus fibrosus.

In some implementations, as shown in FIGS. 15B-15C, the first imaging balloon 228a is inflated with a radiopaque fluid 232 to interrogate the enucleated intervertebral disc cavity 216 for defects and/or contraindications 236 (e.g., tear(s) in the annulus fibrosus, herniations, Schmorl's node, or other end plate defects). As shown in FIG. 15B, first imaging balloon 228a has identified a small tear during the interrogation step. As shown in FIG. 15C, first imaging balloon has identified a herniation and has expanded to extend between and through the herniation during the interrogation step. Once the user determines whether there are any defects and/or contraindications 236 for implanting the spinal implant device 100, the first imaging balloon 228a is removed. In some configurations, first imaging balloon 228a can include an inflatable elastomeric material having a durometer of between Shore 10A to Shore 60A (e.g., Shore 20A). First imaging balloon 228a can be inserted into access cannula 280 and advanced to position the first imaging balloon 228a within the enucleated intervertebral disc cavity 216. Radiopaque fluid 232 (e.g., contrast medium) can be delivered through the first (contrast) lumen 258 to inflate first imaging balloon 228a to a threshold pressure (e.g., 45 psi). The radiopaque fluid 232 can be a substantially incompressible fluid. In some implementations, the threshold pressure is not to exceed 45 psi for confirmation of the integrity of the annulus fibrosus 212. Inflation pressure can be monitored with a pressure monitoring device such as, for example, the QL® inflation device (ATRION® Medical).

Figure 15D:
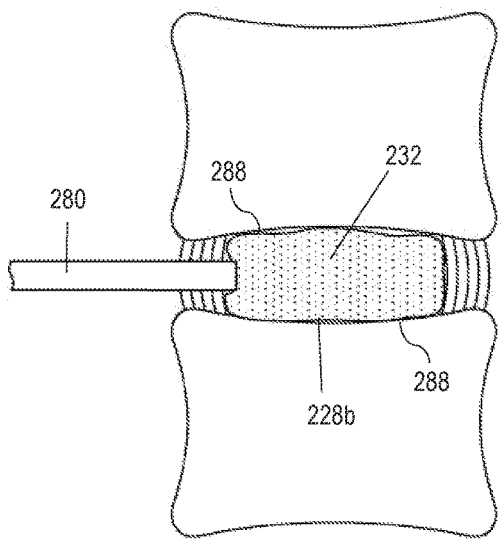
FIG. 15D shows a configuration of a present imaging balloon inflated to fill the enucleated intervertebral disc cavity.

In some implementations, as shown in FIG. 15D, if there are no defects and/or contraindications 236, the method proceeds by inserting a second imaging balloon 228b having a durometer corresponding to a durometer of the spinal implant device 100 or a durometer greater than the durometer of the first imaging balloon 228a; inflating the second imaging balloon 228b with a radiopaque fluid 232 to a threshold pressure; monitoring a volume of the radiopaque fluid 232 to determine an approximate fill volume for the spinal implant device 100; imaging the second imaging balloon 228b to determine a size for the spinal implant device 100; and removing the second imaging balloon 228b. In some configurations, second imaging balloon 228b can include an inflatable elastomeric material having a durometer of between Shore 45A to Shore 55A (e.g., Shore 50A). Second imaging balloon 228b can be inserted into access cannula 280 and advanced to position the second imaging balloon 228b within the enucleated intervertebral disc cavity 216. Radiopaque fluid 232 (e.g., contrast medium) can be delivered through the first (contrast) lumen 258 to inflate second imaging balloon 228b to a threshold pressure (e.g., 30 psi). In some implementations, the threshold pressure is not to exceed 30 psi for using the second imaging balloon 228b as a cross reference during the fill of spinal implant device 100. Inflation pressure can be monitored with a pressure monitoring device such as, for example, the QL® inflation device (ATRION® Medical). In some implementations, the same imaging balloon can be used for assessing the nuclectomy, interrogating the enucleated intervertebral disc cavity 216 for defects and/or contraindications 236, and determining a size and fill volume for the spinal implant device 100. The imaging balloon can have a durometer between Shore 10A and Shore 100A.

In some implementations, the method includes imaging one or more views of the inflated imaging balloon; imaging one or more views of the spinal implant device corresponding to the one or more views imaged of the inflated imaging balloon; and, comparing the one or more views of the spinal implant device with the one or more views of the inflated imaging balloon to assess the spinal implant device. The one or more views of the inflated imaging balloon may be taken in a series of specified views. The one or more views of the imaging balloon and/or the one or more views of the spinal implant device may comprise indicia to quantify congruency between two of the same views. In this way, the position, orientation, and size of the spinal implant device can be confirmed manually. The imaging and comparing steps may also be performed electronically, and may include the step of automatically determining a percentage of overlap between two views. In this way, the position, orientation, and size of the spinal implant device can be confirmed automatically with software suited for determining the percentage of overlap between two views. Using software to automatically image and compare can provide certain advantages such as reduced surgical time and a more effective deployment of the spinal implant device. Further, automatically determining a percentage of overlap between two views can be particularly suited for use with robotic surgery and/or robotics-assisted surgery to insert the spinal implant device. A three-dimensional model may be generated from the first set of views of the imaging balloon and/or the second set of views of the spinal implant device. The three-dimensional model of the imaging balloon and/or the three-dimensional model of the spinal implant device may be used to estimate a fill volume for the spinal implant device. The three-dimensional model of the imaging balloon and/or the three-dimensional model of the spinal implant device may be used to determine a percentage of overlap.

At least some of the present configurations also include a kit for implanting a nuclear prosthesis. The kit can include any configuration of the present spinal implant devices, inflation stylets, plugs, inflation tips, imaging balloons, delivery sheaths, curable materials, spinal disc access devices, spinal implant fill devices, dispenser guns, dual-syringe barrels, mixing tips, and inflation pressure gauges; or, the kit can include any combination of each of the foregoing configurations.

For example, in some configurations a dispenser gun can be configured to couple to the proximal end of the inflation stylet for delivery of a two-part curable silicone material. In some configurations, the curable silicone material 192 is substantially de-gassed prior to delivery into the outer chamber 112. In some configurations, the dispenser gun is a manually activated dispenser providing separated cartridge outlets and mixer inlets, for the delivery of volumetric ratios of material. In this way, the dispenser gun can prevent cross-contamination and premature curing of the curable silicone material 192 in the outlet/inlet area. In some configurations, the dispenser gun is configured to accept a dual-syringe cartridge that contains a first part of a curable medium (e.g., Part A) in a first cartridge and a second part (e.g., Part B) of a curable medium in a second cartridge. In some configurations, a mixing tip can be coupled to the dual-syringe cartridge. In this way, mixing tip can aid in ensuring even mixing of Part A and Part B of the two-part curable silicone material.

The above specification and examples provide a complete description of the structure and use of exemplary configurations. Although certain configurations have been described above with a certain degree of particularity, or with reference to one or more individual configurations, those skilled in the art could make numerous alterations to the disclosed configurations without departing from the scope of this invention. As such, the various illustrative configurations of the present devices, apparatuses, kits, and methods are not intended to be limited to the particular forms disclosed. Rather, they include all modifications and alternatives falling within the scope of the claims, and configurations other than the one shown may include some or all of the features of the depicted configuration. For example, components may be combined as a unitary structure, and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one configuration or may relate to several configurations.

The claims are not intended to include, and should not be interpreted to include, means-plus- or step-plus-function limitations, unless such a limitation is explicitly recited in a given claim using the phrase(s) "means for" or "step for," respectively.

The invention claimed is:
1. A kit for implanting a nuclear prosthesis, the kit comprising:
 a spinal implant device comprising:
  a flexible body defining:
   an outer fillable enclosure defining an outer chamber having a body aperture; and
   an inner fillable enclosure defining an inner chamber such that the outer fillable enclosure at least partially surrounds the inner fillable enclosure, the inner fillable enclosure having an opening in fluid communication with the inner chamber; and a proximal plug configured to be coupled to the inner fillable enclosure such that the proximal plug controls fluid communication through the opening, the proximal plug defines a receptacle including a plug aperture and including a re-sealable membrane to control fluid communication through a proximal opening of the inner chamber, the receptacle including a first retaining element configured to couple with a second retaining element of an inflation stylet, the plug aperture being positioned between the first retaining element and the re-sealable membrane and configured to enable fluid communication to the outer fillable enclosure; and the inflation stylet configured to mate with the proximal plug and extend at least partially through the proximal plug, the inflation stylet comprising:
a first lumen configured to deliver a fluid to and remove a fluid from the inner chamber;
a second lumen surrounding the first lumen and configured to deliver a fluid to the outer chamber; and
the second retaining element configured to control insertion depth of the inflation stylet and to secure the inflation stylet to the proximal plug.

2. The kit of claim 1, where the inflation stylet further comprises an inflation tip for delivering fluid to the outer chamber, the inflation tip configured to be coupled to a distal end of the inflation stylet.

3. The kit of claim 1, where the inner chamber has a proximal end with the proximal opening and a distal end with a distal opening.

4. The kit of claim 1, where the outer fillable enclosure and inner fillable enclosure are axially symmetric around a longitudinal axis.

5. The kit of claim 1, where the inflation stylet further comprises a vent lumen in fluid communication with the second lumen.

6. The kit of claim 1, further comprising one or more imaging balloons configured to assess a nuclectomy, interrogate an enucleated intervertebral disc cavity, and/or determine a size and a fill volume for the spinal implant device.

7. The kit of claim 1, comprising:
a first imaging balloon with a durometer between Shore 10A and Shore 100A; and
a second imaging balloon with a durometer greater than the durometer of the first imaging balloon.

8. The kit of claim 1, further comprising a delivery sheath surrounding the inflation stylet, where the delivery sheath is movable from a delivery position to a deployed position.

9. The kit of claim 1, further comprising one or more of a curable silicone material for injection into the outer chamber, a spinal disc access device, a spinal implant fill device, where the spinal implant fill device comprises a dispenser gun for injecting fluid into the outer chamber, a dual-syringe barrel, a mixing tip, an inflation pressure gauge, or a combination thereof.

10. A spinal implant device comprising:
a flexible body defining:
an outer fillable enclosure defining an outer chamber having a body aperture; and
an inner fillable enclosure defining an inner chamber such that the outer fillable enclosure surrounds the inner fillable enclosure, the inner fillable enclosure having an opening in fluid communication with the inner chamber; and
a proximal plug configured to be coupled to the inner fillable enclosure such that the proximal plug controls fluid communication through the opening, the proximal plug defines a receptacle including a plug aperture and including a re-sealable membrane to control fluid communication through a proximal opening of the inner chamber, the receptacle including a first retaining element configured to couple with a second retaining element of an inflation stylet, the plug aperture being positioned between the first retaining element and the re-sealable membrane and configured to enable fluid communication to the outer fillable enclosure.

11. The spinal implant device of claim 10, where the inner chamber is configured to provide pressure feedback when the outer chamber is filled.

12. The spinal implant device of claim 10, where the flexible body comprises a coating containing one or more ingredients selected from a list of ingredients consisting of: drugs, bioactives, and/or stem cells.

13. The spinal implant device of claim 10, where the inner and outer fillable enclosures comprise a unitary piece of material.

14. The spinal implant device of claim 10, where the inner chamber has a proximal end with a proximal opening and a distal end with a distal opening, and where the outer fillable enclosure and inner fillable enclosure are axially symmetric around a longitudinal axis.

15. The spinal implant device of claim 10, where the flexible body further defines a proximal opening in fluid communication with the inner chamber, a distal opening in fluid communication with the inner chamber, or both.

16. The spinal implant device of claim 15, where the spinal implant device further comprises a distal plug that seals the distal opening.

17. The spinal implant device of claim 10, where the proximal plug defines:
the receptacle configured to receive a portion of the inflation stylet for delivering a fluid to the inner and outer chambers; and
the plug aperture in fluid communication with the outer chamber when aligned with the body aperture.

18. The spinal implant device of claim 17, where the inflation stylet comprises an inflation tip for delivering the fluid to the outer chamber, the inflation tip configured to be coupled to a distal end of the inflation stylet.

19. The spinal implant device of claim 10, where the spinal implant device further comprises a first radiopaque marker coupled to either a distal plug or a portion of the flexible body that is closer to a distal opening of the inner chamber than to the proximal opening of the inner chamber.

20. The spinal implant device of claim 19, where the spinal implant device further comprises a second radiopaque marker coupled to either the proximal plug or a portion of the flexible body that is closer to the proximal opening of the inner chamber than to a distal opening of the inner chamber.

21. The spinal implant device of claim 10, where the outer chamber is filled with a curable medium.

22. The spinal implant device of claim 21, where the curable medium comprises a radiographic material, cures within ten minutes, or both.

23. The spinal implant device of claim 22, where the radiographic material comprises 8 to 16 wt. % of barium sulfate.

24. The spinal implant device of claim 10, wherein the re-sealable membrane has a thickness of between 0.6 mm and 1.0 mm, and wherein the re-sealable membrane is configured to function as a one-way valve and prevent any backflow of fluid from the inner chamber into the outer chamber when a fluid is delivered into the inner chamber.

25. The spinal implant device of claim 10, wherein the second retaining element includes a key or groove, and wherein the second retaining element has a diameter between 1.8 mm and 2.2 mm at a widest point.

* * * * *

UNITED STATES PATENT AND TRADEMARK OFFICE
CERTIFICATE OF CORRECTION

| | |
|---|---|
| PATENT NO. | : 11,744,710 B2 |
| APPLICATION NO. | : 16/560684 |
| DATED | : September 5, 2023 |
| INVENTOR(S) | : W. Loren Francis et al. |

It is certified that error appears in the above-identified patent and that said Letters Patent is hereby corrected as shown below:

In the Specification

Column 1, Line 8, The filing date of Provisional Patent Application No. 62/726,704 should read:
--Sep. 4, 2018.--

Signed and Sealed this
Ninth Day of April, 2024

Katherine Kelly Vidal
*Director of the United States Patent and Trademark Office*